US009621959B2

(12) United States Patent
Mountain

(10) Patent No.: US 9,621,959 B2
(45) Date of Patent: Apr. 11, 2017

(54) IN-RESIDENCE TRACK AND ALERT

(71) Applicant: ECHOSTAR UK HOLDINGS LIMITED, Keighley, West Yorkshire (GB)

(72) Inventor: Dale Llewelyn Mountain, Keighley (GB)

(73) Assignee: EchoStar UK Holdings Limited, Steeton (GB)

( * ) Notice: Subject to any disclaimer, the term of this patent is extended or adjusted under 35 U.S.C. 154(b) by 0 days.

(21) Appl. No.: 14/470,352

(22) Filed: Aug. 27, 2014

(65) Prior Publication Data
US 2016/0066046 A1    Mar. 3, 2016

(51) Int. Cl.
*H04H 60/56*    (2008.01)
*H04N 21/4788*    (2011.01)
(Continued)

(52) U.S. Cl.
CPC ....... *H04N 21/4788* (2013.01); *A61B 5/0022* (2013.01); *G06F 19/3418* (2013.01); *H04H 60/33* (2013.01); *H04N 7/106* (2013.01); *H04N 7/162* (2013.01); *H04N 7/165* (2013.01); *H04N 21/235* (2013.01); *H04N 21/237* (2013.01); *H04N 21/254* (2013.01); *H04N 21/4131* (2013.01); *H04N 21/4223* (2013.01); *H04N 21/4227* (2013.01); *H04N 21/42202* (2013.01); *H04N 21/43615* (2013.01); *H04N 21/44218* (2013.01); *H04N 21/4532* (2013.01); *H04N 21/4622* (2013.01); *H04N 21/478* (2013.01); *H04N 21/4753* (2013.01); *H04N 21/485* (2013.01); *H04N 21/6131* (2013.01);
(Continued)

(58) Field of Classification Search
CPC combination set(s) only.
See application file for complete search history.

(56) References Cited

U.S. PATENT DOCUMENTS 4,386,436 A    5/1983 Kocher et al.
4,581,606 A    4/1986 Mallory
(Continued)

FOREIGN PATENT DOCUMENTS

CA    2 267 988 A1    4/1998
CN    105814555 A    7/2016
(Continued)

OTHER PUBLICATIONS

Jin S H et al., "Intelligent broadcasting system and services for personalized semantic contents consumption", Expert Systems With Applications, Oxford, GB, vol. 31, No. 1, Jul. 1, 2006, pp. 164-173, XP024962718, ISSN: 0957-4174, DOI: 10.1016/J.ESWA.2005.09.021.
(Continued)

*Primary Examiner* — Brian T Pendleton
*Assistant Examiner* — Alexander Gee
(74) *Attorney, Agent, or Firm* — Kilpatrick Townsend & Stockton LLP

(57)  ABSTRACT

Monitoring, via a network of sensors each communicatively coupled to a home gateway system, movement and location of one or more individuals within their own residence. The home gateway system may also respond to inquiries as to a potential or probable or possible status of the one or more individuals within the residence.

20 Claims, 8 Drawing Sheets

(51) Int. Cl.

| | | |
|---|---|---|
| *A61B 5/00* | (2006.01) | |
| *G06F 19/00* | (2011.01) | |
| *H04H 60/33* | (2008.01) | |
| *H04N 7/10* | (2006.01) | |
| *H04N 7/16* | (2011.01) | |
| *H04N 21/235* | (2011.01) | |
| *H04N 21/237* | (2011.01) | |
| *H04N 21/254* | (2011.01) | |
| *H04N 21/436* | (2011.01) | |
| *H04N 21/45* | (2011.01) | |
| *H04N 21/462* | (2011.01) | |
| *H04N 21/475* | (2011.01) | |
| *H04N 21/61* | (2011.01) | |
| *H04N 21/81* | (2011.01) | |
| *H04N 21/41* | (2011.01) | |
| *H04N 21/422* | (2011.01) | |
| *H04N 21/4223* | (2011.01) | |
| *H04N 21/4227* | (2011.01) | |
| *H04N 21/442* | (2011.01) | |
| *H04N 21/478* | (2011.01) | |
| *H04N 21/485* | (2011.01) | |

(52) U.S. Cl.
CPC ....... *H04N 21/6137* (2013.01); *H04N 21/814* (2013.01); *A61B 2503/08* (2013.01)

(56) References Cited

U.S. PATENT DOCUMENTS

| | | |
|---|---|---|
| 4,728,949 A | 3/1988 | Platte et al. |
| 4,959,713 A | 9/1990 | Morotomi et al. |
| 5,400,246 A | 3/1995 | Wilson et al. |
| 5,770,896 A | 6/1998 | Nakajima |
| 5,805,442 A | 9/1998 | Crater et al. |
| 5,822,012 A | 10/1998 | Jeon et al. |
| 5,894,331 A | 4/1999 | Yang |
| 5,926,090 A | 7/1999 | Taylor et al. |
| 5,970,030 A | 10/1999 | Dimitri et al. |
| 6,005,562 A | 12/1999 | Shiga et al. |
| 6,081,758 A | 6/2000 | Parvulescu |
| 6,104,334 A | 8/2000 | Allport |
| 6,107,918 A | 8/2000 | Klein et al. |
| 6,107,935 A | 8/2000 | Comerford et al. |
| 6,119,088 A | 9/2000 | Ciluffo |
| 6,177,931 B1 | 1/2001 | Alexander et al. |
| 6,182,094 B1 | 1/2001 | Humpleman et al. |
| 6,330,621 B1 | 12/2001 | Bakke et al. |
| 6,337,899 B1 | 1/2002 | Alcendor et al. |
| 6,377,858 B1 | 4/2002 | Koeppe |
| 6,405,284 B1 | 6/2002 | Bridge |
| 6,415,257 B1 | 7/2002 | Junqua et al. |
| 6,502,166 B1 | 12/2002 | Cassidy |
| 6,529,230 B1 * | 3/2003 | Chong ............... G08B 25/14 348/14.01 |
| 6,553,375 B1 | 4/2003 | Huang et al. |
| 6,662,282 B2 | 12/2003 | Cochran |
| 6,681,396 B1 | 1/2004 | Bates et al. |
| 6,756,998 B1 | 6/2004 | Bilger |
| 6,931,104 B1 | 8/2005 | Foster et al. |
| 6,976,187 B2 | 12/2005 | Arnott et al. |
| 6,989,731 B1 | 1/2006 | Kawai et al. |
| 7,009,528 B2 | 3/2006 | Griep |
| 7,010,332 B1 | 3/2006 | Irvin et al. |
| 7,088,238 B2 | 8/2006 | Karaoguz et al. |
| 7,103,545 B2 | 9/2006 | Furuta |
| 7,143,298 B2 | 11/2006 | Wells et al. |
| 7,174,512 B2 | 2/2007 | Martin et al. |
| 7,197,715 B1 | 3/2007 | Valeria |
| 7,234,074 B2 | 6/2007 | Cohn et al. |
| 7,260,538 B2 | 8/2007 | Calderone et al. |
| 7,346,917 B2 | 3/2008 | Gatto et al. |
| 7,372,370 B2 | 5/2008 | Stults et al. |
| 7,386,666 B1 | 6/2008 | Beauchamp et al. |
| 7,395,369 B2 | 7/2008 | Sepez et al. |
| 7,395,546 B1 | 7/2008 | Asmussen |
| 7,529,677 B1 | 5/2009 | Wittenberg |
| 7,574,494 B1 | 8/2009 | Mayernick et al. |
| 7,590,703 B2 | 9/2009 | Cashman et al. |
| 7,633,887 B2 | 12/2009 | Panwar et al. |
| 7,640,351 B2 | 12/2009 | Reckamp et al. |
| 7,680,894 B2 | 3/2010 | Diot et al. |
| 7,694,005 B2 | 4/2010 | Reckamp et al. |
| 7,739,718 B1 | 6/2010 | Young et al. |
| 7,774,811 B2 | 8/2010 | Poslinski et al. |
| 7,818,368 B2 | 10/2010 | Yang et al. |
| 7,825,989 B1 | 11/2010 | Greenberg |
| 7,849,487 B1 | 12/2010 | Vosseller |
| 7,861,034 B2 | 12/2010 | Yamamoto et al. |
| 7,870,232 B2 | 1/2011 | Reckamp et al. |
| 7,945,297 B2 | 5/2011 | Philipp |
| 7,969,318 B2 | 6/2011 | White et al. |
| 8,013,730 B2 | 9/2011 | Oh et al. |
| 8,046,798 B1 | 10/2011 | Schlack et al. |
| 8,079,052 B2 | 12/2011 | Chen et al. |
| 8,086,757 B2 | 12/2011 | Chang |
| 8,104,065 B2 | 1/2012 | Aaby et al. |
| 8,106,768 B2 | 1/2012 | Neumann |
| 8,156,368 B2 | 4/2012 | Chambliss et al. |
| 8,171,148 B2 | 5/2012 | Lucas et al. |
| 8,180,735 B2 | 5/2012 | Ansari et al. |
| 8,201,261 B2 | 6/2012 | Barfield et al. |
| 8,209,713 B2 | 6/2012 | Lai et al. |
| 8,221,290 B2 | 7/2012 | Vincent et al. |
| 8,275,143 B2 | 9/2012 | Johnson |
| 8,289,157 B2 | 10/2012 | Patenaude et al. |
| 8,290,545 B2 | 10/2012 | Terlizzi |
| 8,296,797 B2 | 10/2012 | Olstad et al. |
| 8,310,335 B2 | 11/2012 | Sivakkolundhu |
| 8,312,486 B1 | 11/2012 | Briggs et al. |
| 8,316,413 B2 | 11/2012 | Crabtree |
| 8,320,578 B2 | 11/2012 | Kahn et al. |
| 8,335,312 B2 | 12/2012 | Gerhardt et al. |
| 8,413,204 B2 | 4/2013 | White et al. |
| 8,424,041 B2 | 4/2013 | Candelore et al. |
| 8,498,572 B1 | 7/2013 | Schooley et al. |
| 8,516,087 B2 | 8/2013 | Wilson et al. |
| 8,550,368 B2 | 10/2013 | Butler et al. |
| 8,619,136 B2 | 12/2013 | Howarter et al. |
| 8,644,525 B2 | 2/2014 | Bathurst et al. |
| 8,645,327 B2 | 2/2014 | Falkenburg et al. |
| 8,689,258 B2 | 4/2014 | Kemp |
| 8,750,576 B2 | 6/2014 | Huang et al. |
| 8,752,084 B1 | 6/2014 | Lai et al. |
| 8,780,201 B1 | 7/2014 | Scalisi et al. |
| 8,786,698 B2 | 7/2014 | Chen et al. |
| 8,799,413 B2 | 8/2014 | Taylor et al. |
| 8,898,709 B2 | 11/2014 | Crabtree |
| 8,930,700 B2 | 1/2015 | Wielopolski |
| 8,965,170 B1 | 2/2015 | Benea et al. |
| 8,973,038 B2 | 3/2015 | Gratton |
| 8,973,068 B2 | 3/2015 | Kotecha et al. |
| 8,990,418 B1 | 3/2015 | Bragg et al. |
| 9,019,111 B1 | 4/2015 | Sloo et al. |
| 9,038,127 B2 | 5/2015 | Hastings et al. |
| 9,049,567 B2 | 6/2015 | Le Guen et al. |
| 9,066,156 B2 | 6/2015 | Kapa, Jr. |
| 9,213,986 B1 | 12/2015 | Buchheit et al. |
| 9,246,921 B1 | 1/2016 | Vlaminck et al. |
| 9,253,533 B1 | 2/2016 | Morgan et al. |
| 9,420,333 B2 | 8/2016 | Martch et al. |
| 9,462,041 B1 | 10/2016 | Hagins et al. |
| 9,495,860 B2 | 11/2016 | Lett |
| 2001/0012998 A1 | 8/2001 | Jouet et al. |
| 2001/0013123 A1 | 8/2001 | Freeman et al. |
| 2001/0026609 A1 | 10/2001 | Weinstein et al. |
| 2002/0019725 A1 | 2/2002 | Petite |
| 2002/0059610 A1 | 5/2002 | Ellis |
| 2002/0063633 A1 | 5/2002 | Park |
| 2002/0067376 A1 | 6/2002 | Martin et al. |
| 2002/0075402 A1 | 6/2002 | Robson et al. |
| 2002/0178444 A1 | 11/2002 | Trajkovic et al. |

(56) References Cited

U.S. PATENT DOCUMENTS

| | | |
|---|---|---|
| 2002/0193989 A1 | 12/2002 | Geilhufe et al. |
| 2003/0005431 A1 | 1/2003 | Shinohara |
| 2003/0023742 A1 | 1/2003 | Allen et al. |
| 2003/0052789 A1 | 3/2003 | Colmenarez et al. |
| 2003/0056220 A1 | 3/2003 | Thornton et al. |
| 2003/0066077 A1 | 4/2003 | Gutta et al. |
| 2003/0097452 A1 | 5/2003 | Kim et al. |
| 2003/0118014 A1 | 6/2003 | Iyer et al. |
| 2003/0126593 A1 | 7/2003 | Mault |
| 2003/0126605 A1 | 7/2003 | Betz et al. |
| 2003/0126606 A1 | 7/2003 | Buczak et al. |
| 2003/0133551 A1 | 7/2003 | Kahn |
| 2003/0140352 A1 | 7/2003 | Kim |
| 2003/0188317 A1 | 10/2003 | Liew et al. |
| 2003/0189674 A1 | 10/2003 | Inoue et al. |
| 2003/0201900 A1 | 10/2003 | Bachinski et al. |
| 2003/0208763 A1 | 11/2003 | McElhatten et al. |
| 2003/0229899 A1 | 12/2003 | Thompson et al. |
| 2004/0019489 A1* | 1/2004 | Funk ............... H04L 12/2803 704/275 |
| 2004/0117038 A1 | 6/2004 | Karaoguz et al. |
| 2004/0117843 A1 | 6/2004 | Karaoguz et al. |
| 2004/0121725 A1 | 6/2004 | Matsui |
| 2004/0128034 A1 | 7/2004 | Lenker et al. |
| 2004/0143838 A1 | 7/2004 | Rose |
| 2004/0148419 A1 | 7/2004 | Chen et al. |
| 2004/0148632 A1 | 7/2004 | Park et al. |
| 2004/0181807 A1 | 9/2004 | Theiste et al. |
| 2004/0260407 A1 | 12/2004 | Wimsatt |
| 2004/0266419 A1 | 12/2004 | Arling et al. |
| 2005/0030977 A1 | 2/2005 | Casey et al. |
| 2005/0038875 A1 | 2/2005 | Park |
| 2005/0044570 A1 | 2/2005 | Poslinski |
| 2005/0049862 A1 | 3/2005 | Choi et al. |
| 2005/0071865 A1 | 3/2005 | Martins |
| 2005/0125302 A1 | 6/2005 | Brown et al. |
| 2005/0152565 A1 | 7/2005 | Jouppi et al. |
| 2005/0166230 A1 | 7/2005 | Gaydou et al. |
| 2005/0188315 A1 | 8/2005 | Campbell et al. |
| 2005/0191041 A1 | 9/2005 | Braun et al. |
| 2005/0200478 A1 | 9/2005 | Koch et al. |
| 2005/0240961 A1 | 10/2005 | Jerding et al. |
| 2005/0245292 A1 | 11/2005 | Bennett et al. |
| 2005/0264698 A1 | 12/2005 | Eshleman |
| 2005/0264705 A1 | 12/2005 | Kitamura |
| 2005/0289614 A1 | 12/2005 | Baek et al. |
| 2006/0011145 A1 | 1/2006 | Kates |
| 2006/0087428 A1 | 4/2006 | Wolfe et al. |
| 2006/0136968 A1 | 6/2006 | Han et al. |
| 2006/0143679 A1 | 6/2006 | Yamada et al. |
| 2006/0155389 A1 | 7/2006 | Pessolano et al. |
| 2006/0174277 A1 | 8/2006 | Sezan et al. |
| 2006/0190615 A1 | 8/2006 | Panwar et al. |
| 2006/0238656 A1 | 10/2006 | Chen et al. |
| 2006/0253581 A1 | 11/2006 | Dixon et al. |
| 2006/0282852 A1 | 12/2006 | Purpura et al. |
| 2006/0282869 A1 | 12/2006 | Plourde, Jr. |
| 2007/0033616 A1 | 2/2007 | Gutta |
| 2007/0044119 A1 | 2/2007 | Sullivan et al. |
| 2007/0058930 A1 | 3/2007 | Iwamoto |
| 2007/0078910 A1 | 4/2007 | Bopardikar |
| 2007/0083901 A1 | 4/2007 | Bond |
| 2007/0127894 A1 | 6/2007 | Ando et al. |
| 2007/0129220 A1 | 6/2007 | Bardha |
| 2007/0142022 A1 | 6/2007 | Madonna et al. |
| 2007/0146545 A1 | 6/2007 | Iwahashi |
| 2007/0146554 A1 | 6/2007 | Strickland et al. |
| 2007/0154163 A1 | 7/2007 | Cordray |
| 2007/0154169 A1 | 7/2007 | Cordray et al. |
| 2007/0157235 A1 | 7/2007 | Teunissen |
| 2007/0157249 A1 | 7/2007 | Cordray et al. |
| 2007/0157253 A1 | 7/2007 | Ellis et al. |
| 2007/0157258 A1 | 7/2007 | Jung et al. |
| 2007/0188655 A1 | 8/2007 | Ohta |
| 2007/0192486 A1 | 8/2007 | Wilson et al. |
| 2007/0199040 A1 | 8/2007 | Kates |
| 2007/0204302 A1 | 8/2007 | Calzone |
| 2007/0226766 A1 | 9/2007 | Poslinski et al. |
| 2007/0245379 A1 | 10/2007 | Agnihortri |
| 2007/0256085 A1 | 11/2007 | Reckamp et al. |
| 2007/0271518 A1 | 11/2007 | Tischer et al. |
| 2007/0275670 A1 | 11/2007 | Chen et al. |
| 2008/0021971 A1 | 1/2008 | Halgas |
| 2008/0022012 A1 | 1/2008 | Wang |
| 2008/0022322 A1 | 1/2008 | Grannan et al. |
| 2008/0060006 A1 | 3/2008 | Shanks et al. |
| 2008/0062258 A1 | 3/2008 | Bentkovski et al. |
| 2008/0062965 A1 | 3/2008 | Silva et al. |
| 2008/0086743 A1 | 4/2008 | Cheng et al. |
| 2008/0097949 A1 | 4/2008 | Kelly et al. |
| 2008/0109095 A1 | 5/2008 | Braithwaite et al. |
| 2008/0109307 A1 | 5/2008 | Ullah |
| 2008/0114963 A1 | 5/2008 | Cannon et al. |
| 2008/0123825 A1* | 5/2008 | Abramson ............... H04M 3/38 379/93.02 |
| 2008/0134043 A1 | 6/2008 | Georgis et al. |
| 2008/0140736 A1 | 6/2008 | Jarno |
| 2008/0163305 A1 | 7/2008 | Johnson et al. |
| 2008/0163330 A1 | 7/2008 | Sparrell |
| 2008/0195457 A1 | 8/2008 | Sherman et al. |
| 2008/0235348 A1 | 9/2008 | Dasgupta |
| 2008/0239169 A1 | 10/2008 | Moon et al. |
| 2008/0278635 A1 | 11/2008 | Hardacker et al. |
| 2008/0284905 A1 | 11/2008 | Chuang |
| 2008/0288876 A1 | 11/2008 | Fleming |
| 2008/0297660 A1 | 12/2008 | Shioya |
| 2008/0300982 A1 | 12/2008 | Larson et al. |
| 2008/0320523 A1 | 12/2008 | Morris et al. |
| 2009/0044217 A1 | 2/2009 | Lutterbach et al. |
| 2009/0055385 A1 | 2/2009 | Jeon et al. |
| 2009/0069038 A1 | 3/2009 | Olague et al. |
| 2009/0102984 A1 | 4/2009 | Arling et al. |
| 2009/0138507 A1 | 5/2009 | Burckart et al. |
| 2009/0146834 A1 | 6/2009 | Huang |
| 2009/0165069 A1 | 6/2009 | Kirchner |
| 2009/0167555 A1 | 7/2009 | Kohanek |
| 2009/0178071 A1 | 7/2009 | Whitehead |
| 2009/0190040 A1 | 7/2009 | Watanabe et al. |
| 2009/0234828 A1 | 9/2009 | Tu |
| 2009/0249412 A1 | 10/2009 | Bhogal et al. |
| 2009/0249428 A1 | 10/2009 | White et al. |
| 2009/0271203 A1 | 10/2009 | Resch et al. |
| 2009/0293093 A1 | 11/2009 | Igarashi |
| 2009/0299824 A1 | 12/2009 | Barnes, Jr. |
| 2009/0325523 A1 | 12/2009 | Choi |
| 2010/0031286 A1 | 2/2010 | Gupta et al. |
| 2010/0040151 A1 | 2/2010 | Garrett |
| 2010/0046918 A1 | 2/2010 | Takao et al. |
| 2010/0071007 A1 | 3/2010 | Meijer |
| 2010/0071062 A1 | 3/2010 | Choyi et al. |
| 2010/0083371 A1 | 4/2010 | Bennetts et al. |
| 2010/0089996 A1 | 4/2010 | Koplar |
| 2010/0097225 A1 | 4/2010 | Petricoin, Jr. |
| 2010/0115554 A1 | 5/2010 | Drouet et al. |
| 2010/0122284 A1 | 5/2010 | Yoon et al. |
| 2010/0122294 A1 | 5/2010 | Craner |
| 2010/0131280 A1 | 5/2010 | Bogineni |
| 2010/0138007 A1 | 6/2010 | Clark et al. |
| 2010/0138858 A1 | 6/2010 | Velazquez et al. |
| 2010/0146445 A1 | 6/2010 | Kraut |
| 2010/0146560 A1 | 6/2010 | Bonfrer |
| 2010/0153983 A1 | 6/2010 | Philmon et al. |
| 2010/0153999 A1 | 6/2010 | Yates |
| 2010/0166389 A1 | 7/2010 | Knee et al. |
| 2010/0169925 A1 | 7/2010 | Takegoshi |
| 2010/0211546 A1 | 8/2010 | Grohman et al. |
| 2010/0217613 A1 | 8/2010 | Kelly |
| 2010/0218214 A1 | 8/2010 | Fan et al. |
| 2010/0251295 A1 | 9/2010 | Amento et al. |
| 2010/0262986 A1 | 10/2010 | Adimatyam et al. |
| 2010/0269144 A1 | 10/2010 | Forsman et al. |
| 2010/0283579 A1 | 11/2010 | Kraus et al. |
| 2010/0319019 A1 | 12/2010 | Zazza |
| 2010/0321151 A1 | 12/2010 | Matsuura et al. |

(56) References Cited

U.S. PATENT DOCUMENTS

| | | |
|---|---|---|
| 2010/0322592 A1 | 12/2010 | Casagrande |
| 2010/0333131 A1 | 12/2010 | Parker et al. |
| 2011/0016492 A1 | 1/2011 | Morita |
| 2011/0019839 A1 | 1/2011 | Nandury |
| 2011/0030016 A1 | 2/2011 | Pino et al. |
| 2011/0032423 A1 | 2/2011 | Jing et al. |
| 2011/0052156 A1 | 3/2011 | Kuhn |
| 2011/0072448 A1 | 3/2011 | Stiers et al. |
| 2011/0093126 A1 | 4/2011 | Toba et al. |
| 2011/0109801 A1 | 5/2011 | Thomas et al. |
| 2011/0119325 A1 | 5/2011 | Paul et al. |
| 2011/0150432 A1 | 6/2011 | Paul et al. |
| 2011/0156862 A1 | 6/2011 | Langer |
| 2011/0187928 A1 | 8/2011 | Crabtree |
| 2011/0187930 A1 | 8/2011 | Crabtree |
| 2011/0187931 A1 | 8/2011 | Kim |
| 2011/0202956 A1 | 8/2011 | Connelly et al. |
| 2011/0206342 A1 | 8/2011 | Thompson et al. |
| 2011/0243533 A1 | 10/2011 | Stern et al. |
| 2011/0252451 A1 | 10/2011 | Turgeman et al. |
| 2011/0270549 A1 | 11/2011 | Jeansonne et al. |
| 2011/0282837 A1 | 11/2011 | Gounares et al. |
| 2011/0283311 A1 | 11/2011 | Luong |
| 2011/0286721 A1 | 11/2011 | Craner |
| 2011/0289410 A1 | 11/2011 | Paczkowski et al. |
| 2011/0293113 A1 | 12/2011 | McCarthy |
| 2011/0295396 A1 | 12/2011 | Chinen et al. |
| 2012/0019388 A1 | 1/2012 | Kates |
| 2012/0020641 A1 | 1/2012 | Sakaniwa et al. |
| 2012/0047532 A1 | 2/2012 | McCarthy |
| 2012/0052941 A1 | 3/2012 | Mo |
| 2012/0059495 A1 | 3/2012 | Weiss et al. |
| 2012/0060178 A1 | 3/2012 | Minakuchi et al. |
| 2012/0069246 A1 | 3/2012 | Thornberry et al. |
| 2012/0094696 A1 | 4/2012 | Ahn et al. |
| 2012/0106932 A1 | 5/2012 | Grevers, Jr. |
| 2012/0124456 A1 | 5/2012 | Perez et al. |
| 2012/0131613 A1 | 5/2012 | Ellis et al. |
| 2012/0154108 A1 | 6/2012 | Sugaya |
| 2012/0185895 A1 | 7/2012 | Wong et al. |
| 2012/0204209 A1 | 8/2012 | Kubo |
| 2012/0230651 A1 | 9/2012 | Chen |
| 2012/0246672 A1 | 9/2012 | Sridhar et al. |
| 2012/0271670 A1 | 10/2012 | Zaloom |
| 2012/0278837 A1 | 11/2012 | Curtis et al. |
| 2012/0280802 A1 | 11/2012 | Yoshida et al. |
| 2012/0291068 A1 | 11/2012 | Khushoo et al. |
| 2012/0311633 A1 | 12/2012 | Mandrekar et al. |
| 2012/0316876 A1 | 12/2012 | Jang et al. |
| 2012/0326835 A1 | 12/2012 | Cockrell et al. |
| 2013/0046800 A1 | 2/2013 | Assi et al. |
| 2013/0053063 A1 | 2/2013 | McSheffrey |
| 2013/0055304 A1 | 2/2013 | Kirby et al. |
| 2013/0060358 A1 | 3/2013 | Li et al. |
| 2013/0061313 A1 | 3/2013 | Cullimore et al. |
| 2013/0070044 A1 | 3/2013 | Naidoo et al. |
| 2013/0074061 A1 | 3/2013 | Averbuch et al. |
| 2013/0074109 A1 | 3/2013 | Skelton et al. |
| 2013/0090213 A1 | 4/2013 | Amini et al. |
| 2013/0114940 A1 | 5/2013 | Merzon et al. |
| 2013/0128119 A1 | 5/2013 | Madathodiyil et al. |
| 2013/0138757 A1 | 5/2013 | Ferron |
| 2013/0145023 A1 | 6/2013 | Li et al. |
| 2013/0152139 A1 | 6/2013 | Davis et al. |
| 2013/0174196 A1 | 7/2013 | Herlein |
| 2013/0194503 A1 | 8/2013 | Yamashita |
| 2013/0204408 A1 | 8/2013 | Thiruvengada et al. |
| 2013/0263189 A1 | 10/2013 | Garner |
| 2013/0267383 A1 | 10/2013 | Watterson |
| 2013/0283162 A1 | 10/2013 | Aronsson et al. |
| 2013/0298151 A1 | 11/2013 | Leske et al. |
| 2013/0300576 A1 | 11/2013 | Sinsuan et al. |
| 2013/0318559 A1 | 11/2013 | Crabtree |
| 2013/0321637 A1 | 12/2013 | Frank et al. |
| 2013/0324247 A1 | 12/2013 | Esaki et al. |
| 2013/0332962 A1 | 12/2013 | Moritz et al. |
| 2013/0346302 A1 | 12/2013 | Purves et al. |
| 2014/0032709 A1 | 1/2014 | Saussy et al. |
| 2014/0068675 A1 | 3/2014 | Mountain |
| 2014/0095684 A1 | 4/2014 | Nonaka et al. |
| 2014/0101465 A1 | 4/2014 | Wang et al. |
| 2014/0123160 A1 | 5/2014 | van Coppenolle et al. |
| 2014/0139555 A1 | 5/2014 | Levy |
| 2014/0140680 A1 | 5/2014 | Jo |
| 2014/0153904 A1 | 6/2014 | Adimatyam et al. |
| 2014/0157327 A1 | 6/2014 | Roberts et al. |
| 2014/0160360 A1 | 6/2014 | Hsu et al. |
| 2014/0168277 A1 | 6/2014 | Ashley et al. |
| 2014/0192197 A1 | 7/2014 | Hanko et al. |
| 2014/0192997 A1 | 7/2014 | Niu et al. |
| 2014/0215505 A1 | 7/2014 | Balasubramanian et al. |
| 2014/0215539 A1 | 7/2014 | Chen et al. |
| 2014/0218517 A1* | 8/2014 | Kim .................. H04L 12/2818 348/143 |
| 2014/0266669 A1 | 9/2014 | Fadell et al. |
| 2014/0266684 A1 | 9/2014 | Poder et al. |
| 2014/0282714 A1 | 9/2014 | Hussain |
| 2014/0282741 A1 | 9/2014 | Shoykhet |
| 2014/0282745 A1 | 9/2014 | Chipman et al. |
| 2014/0282759 A1 | 9/2014 | Harvey et al. |
| 2014/0294201 A1 | 10/2014 | Johnson et al. |
| 2014/0310075 A1* | 10/2014 | Ricci .................. H04W 48/04 705/13 |
| 2014/0310819 A1 | 10/2014 | Cakarel et al. |
| 2014/0313341 A1 | 10/2014 | Stribling |
| 2014/0325556 A1 | 10/2014 | Hoang et al. |
| 2014/0331260 A1 | 11/2014 | Gratton |
| 2014/0333529 A1 | 11/2014 | Kim et al. |
| 2014/0333841 A1 | 11/2014 | Steck |
| 2014/0351832 A1 | 11/2014 | Cho et al. |
| 2014/0362201 A1 | 12/2014 | Nguyen et al. |
| 2014/0373074 A1 | 12/2014 | Hwang et al. |
| 2014/0373079 A1 | 12/2014 | Friedrich et al. |
| 2015/0003814 A1 | 1/2015 | Miller |
| 2015/0020097 A1 | 1/2015 | Freed et al. |
| 2015/0029096 A1 | 1/2015 | Ishihara |
| 2015/0054910 A1* | 2/2015 | Offen .................. H04M 3/42059 348/14.02 |
| 2015/0058890 A1 | 2/2015 | Kapa |
| 2015/0084770 A1 | 3/2015 | Xiao et al. |
| 2015/0095932 A1 | 4/2015 | Ren |
| 2015/0106866 A1 | 4/2015 | Fujita |
| 2015/0118992 A1 | 4/2015 | Wyatt et al. |
| 2015/0143408 A1* | 5/2015 | Sallas .................. H04N 21/814 725/33 |
| 2015/0156612 A1* | 6/2015 | Vemulapalli .......... H04W 4/043 455/456.1 |
| 2015/0159401 A1 | 6/2015 | Patrick et al. |
| 2015/0160623 A1 | 6/2015 | Holley |
| 2015/0160634 A1 | 6/2015 | Smith et al. |
| 2015/0160635 A1 | 6/2015 | Schofield et al. |
| 2015/0160636 A1 | 6/2015 | McCarthy et al. |
| 2015/0160663 A1 | 6/2015 | McCarthy et al. |
| 2015/0161452 A1 | 6/2015 | McCarthy et al. |
| 2015/0161882 A1 | 6/2015 | Lett |
| 2015/0162006 A1 | 6/2015 | Kummer |
| 2015/0163411 A1 | 6/2015 | McCarthy, III et al. |
| 2015/0163412 A1 | 6/2015 | Holley et al. |
| 2015/0163535 A1 | 6/2015 | McCarthy et al. |
| 2015/0172742 A1 | 6/2015 | Richardson |
| 2015/0181132 A1 | 6/2015 | Kummer et al. |
| 2015/0181279 A1 | 6/2015 | Martch et al. |
| 2015/0249803 A1 | 9/2015 | Tozer et al. |
| 2015/0249864 A1 | 9/2015 | Tang et al. |
| 2015/0281824 A1 | 10/2015 | Nguyen et al. |
| 2015/0309487 A1 | 10/2015 | Lyman |
| 2015/0310725 A1 | 10/2015 | Koskan et al. |
| 2016/0063854 A1 | 3/2016 | Burton et al. |
| 2016/0066020 A1 | 3/2016 | Mountain |
| 2016/0066026 A1 | 3/2016 | Mountain |
| 2016/0066049 A1 | 3/2016 | Mountain |
| 2016/0066056 A1 | 3/2016 | Mountain |
| 2016/0073172 A1 | 3/2016 | Sharples |
| 2016/0088351 A1 | 3/2016 | Petruzzelli et al. |

(56) References Cited

U.S. PATENT DOCUMENTS

| | | |
|---|---|---|
| 2016/0091471 A1 | 3/2016 | Benn |
| 2016/0109864 A1 | 4/2016 | Lonn |
| 2016/0121161 A1 | 5/2016 | Mountain |
| 2016/0123741 A1 | 5/2016 | Mountain |
| 2016/0163168 A1 | 6/2016 | Brav et al. |
| 2016/0182249 A1 | 6/2016 | Lea |
| 2016/0191147 A1 | 6/2016 | Martch |
| 2016/0191912 A1 | 6/2016 | Lea et al. |
| 2016/0191990 A1 | 6/2016 | McCarthy |
| 2016/0198229 A1 | 7/2016 | Keipert |
| 2016/0203700 A1 | 7/2016 | Bruhn et al. |
| 2016/0286327 A1 | 9/2016 | Marten |
| 2016/0309212 A1 | 10/2016 | Martch et al. |

FOREIGN PATENT DOCUMENTS

| | | |
|---|---|---|
| EP | 1 865 716 A2 | 12/2007 |
| EP | 2 309 733 B1 | 4/2011 |
| EP | 2 403 239 A1 | 1/2012 |
| EP | 2 736 027 A1 | 5/2014 |
| EP | 3 080 677 A1 | 10/2016 |
| EP | 3 080 710 A1 | 10/2016 |
| FR | 2 902 568 A1 | 12/2007 |
| GB | 2 304 952 A | 3/1997 |
| JP | H10 322622 A | 12/1998 |
| JP | 2006-245745 A | 9/2006 |
| JP | 2008148016 A | 6/2008 |
| KR | 2004 0025073 A | 3/2004 |
| KR | 2006 0128295 A | 12/2006 |
| WO | 93/20544 A1 | 10/1993 |
| WO | 98/37694 A1 | 8/1998 |
| WO | 2004/068386 A1 | 8/2004 |
| WO | 2005/059807 A2 | 6/2005 |
| WO | 2007/064987 A2 | 6/2007 |
| WO | 2007/098067 A1 | 8/2007 |
| WO | 2009/073925 A1 | 6/2009 |
| WO | 2011/095567 A1 | 8/2011 |
| WO | 2013/016626 A1 | 1/2013 |
| WO | 2014/068556 A1 | 5/2014 |
| WO | 2014/072742 A1 | 5/2014 |
| WO | 2014/179017 A1 | 11/2014 |
| WO | 2016/030384 | 3/2016 |
| WO | 2016/030477 A1 | 3/2016 |
| WO | 2016/034880 A1 | 3/2016 |
| WO | 2016/034899 A1 | 3/2016 |
| WO | 2016/055761 A1 | 4/2016 |
| WO | 2016/066399 A1 | 5/2016 |
| WO | 2016/066442 A1 | 5/2016 |

OTHER PUBLICATIONS

Sung Ho Jin et al., "Real-time content filtering for live broadcasts in TV terminals", Multimedia Tools and Applications, Kluwer Academic Publishers, BO, vol. 36, No. 3, Jun. 29, 2007 pp. 285-301, XP019578768, ISSN: 1573-7721.
Wang et al., "Mixed Sound Event Verification on Wireless Sensor Network for Home Automation," IEEE Transactions on Industrial Informatics, vol. 10, No. 1, Feb. 2014, 10 pages.
European Search Report for EP 14197940.1 mailed Apr. 28, 2015, 13 pages.
Mexican Institute of Industrial Property Office Action dated Nov. 1, 2013, for Mex. Patent Appln No. MX/a/2012/008882 is not translated into English, 3 pages.
Mexican Institute of Industrial Property Notice of Allowance dated Feb. 10, 2014, for Mex. Patent Appln No. MX/a/2012/008882, 1 page.
U.S. Appl. No. 12/700,310, filed Feb. 4, 2010 Non-Final Office Action mailed Mar. 11, 2015, 35 pages.
U.S. Appl. No. 13/919,702, filed Jun. 17, 2013 Non-Final Office Action mailed Apr. 30, 2015, 26 pages.
U.S. Appl. No. 13/942,451, filed Jul. 15, 2013 Final Office Action mailed Apr. 30, 2015, 33 pages.
U.S. Appl. No. 13/971,579, filed Aug. 20, 2013 Notice of Allowance mailed Feb. 27, 2015, 28 pages.
U.S. Appl. No. 14/071,613, filed Nov. 4, 2013 Non-Final Office Action mailed May 18, 2015, 20 pages.
U.S. Appl. No. 14/107,132, filed Dec. 16, 2013 Non Final Office Action mailed May 27, 2015, 26 pages.
U.S. Appl. No. 14/139,420, filed Dec. 23, 2013 Non-Final Office Action mailed Apr. 30, 2015, 27 pages.
U.S. Appl. No. 14/200,864, filed Mar. 7, 2014 Final Office Action mailed Jun. 18, 2015, 36 pages.
U.S. Appl. No. 14/485,188, filed Sep. 12, 2014, Pre-Interview First Office Action mailed Jul. 29, 2015, 20 pages.
U.S. Appl. No. 14/485,188, filed Sep. 12, 2014, Pre-Interview First Office Action mailed Oct. 1, 2015, 10 pages.
U.S. Appl. No. 14/139,299, filed Dec. 23, 2013, Non Final Office Action mailed Aug. 14, 2015, 39 pages.
U.S. Appl. No. 14/470,248, filed Aug. 27, 2014, Preinterview first office action mailed Sep. 4, 2015, 22 pages.
U.S. Appl. No. 14/470,279, filed Aug. 27, 2014, Preinterview first office action mailed Aug. 26, 2015, 23 pages.
U.S. Appl. No. 14/479,007 filed Sep. 5, 2014, Non-Final Office Action mailed Sep. 1, 2015, 44 pages.
"Acoustic/Ultrasound Ultrasonic Flowmeter Basics," Questex Media Group LLC, accessed on Dec. 16, 2014, 4 pages. Retrieved from http://www.sensorsmag.com/sensors/acoustic-ultrasound/ultrasonic-flowmeter-basics-842.
"AllJoyn Onboarding Service Frameworks," Qualcomm Connected Experiences, Inc., accessed on Jul. 15, 2014, 9 pages. Retrieved from https://www.alljoyn.org.
"App for Samsung Smart TV®," Crestron Electronics, Inc., accessed on Jul. 14, 2014, 3 pages. Retrieved from http://www.crestron.com/products/smart tv television apps/.
"Do you want to know how to find water leaks? Use a Bravedo Water Alert Flow Monitor to find out!", Bravedo.com, accessed Dec. 16, 2014, 10 pages. Retrieved from http://bravedo.com/.
"Flow Pulse®, Non-invasive clamp-on flow monitor for pipes," Pulsar Process Measurement Ltd, accessed on Dec. 16, 2014, 2 pages. Retrieved from http://www.pulsar-pm.com/product-types/flow/flow-pulse.aspx.
"International Building Code Excerpts, Updated with recent code changes that impact electromagnetic locks," Securitron, Assa Abloy, 2007, 2009,2 pages.Retrieved from: www.securitron.com/Other/.../New_IBC-IFC_Code_Language.pdf.
"Introduction to Ultrasonic Doppler Flowmeters," OMEGA Engineering inc., accessed on Dec. 16, 2014, 3 pages. Retrieved from http://www.omega.com/prodinfo/ultrasonicflowmeters.html.
"Ultrasonic Flow Meters," RS Hydro Ltd, accessed on Dec. 16, 2014, 3 pages. Retrieved from http://www.rshydro.co.uk/ultrasonic-flowmeter.shtml.
"Voice Activated TV using the Amulet Remote for Media Center," AmuletDevices.com, accessed on Jul. 14, 2014, 1 page. Retrieved from http://www.amuletdevices.com/index.php/Features/television.html.
Lamonica, M., "CES 2010 Preview: Green comes in many colors," retrieved from CNET.com (http://ces.cnet.com/8301-31045_1-10420381-269.html), Dec. 22, 2009, 2 pages.
Robbins, Gordon, Deputy Chief, "Addison Fire Department Access Control Installation," 2006 International Fire Code, Section 1008.1.3.4, 4 pages.
Extended European Search Report for EP 11166892.7 dated Oct. 6, 2011, 7 pages.
Extended European Search Report for EP 14160140.1 received Jul. 7, 2014, 7 pages.
International Search Report and Written Opinion for PCT/US2014/033796 mailed Sep. 5, 2014, 12 pages.
International Search Report and Written Opinion for PCT/EP2011/051608 mailed on May 30, 2011, 13 pages.
International Preliminary Report on Patentability for PCT/EP2011/051608 mailed Aug. 16, 2012, 8 pages.
International Search Report and Written Opinion for PCT/US2014/053876 mailed Nov. 26, 2014, 8 pages.
International Search Report and Written Opinion for PCT/US2014/055441 mailed Dec. 4, 2014, 10 pages.

(56) References Cited

OTHER PUBLICATIONS

International Search Report and Written Opinion for PCT/US2014/055476 mailed Dec. 30, 2014, 10 pages.
The Office Action for Mexican Patent Application No. MX/a/2012/008882 dated Dec. 16, 2013, is not translated into English, 3 pages.
U.S. Appl. No. 12/700,310, filed Feb. 4, 2010 Office Action mailed May 4, 2012, 15 pages.
U.S. Appl. No. 12/700,310, filed Feb. 4, 2010 Final Office Action mailed Oct. 10, 2012, 16 pages.
U.S. Appl. No. 12/700,310, filed Feb. 4, 2010 Non-Final Office Action mailed Apr. 1, 2013, 16 pages.
U.S. Appl. No. 12/700,310, filed Feb. 4, 2010 Non-Final Office Action mailed Oct. 15, 2013, 15 pages.
U.S. Appl. No. 12/700,310, filed Feb. 4, 2010 Final Office Action mailed Feb. 28, 2014, 17 pages.
U.S. Appl. No. 12/700,310, filed Feb. 4, 2010 Non-Final Office Action mailed Aug. 14, 2014, 18 pages.
U.S. Appl. No. 12/700,408, filed Feb. 4, 2010 Notice of Allowance mailed Jul. 28, 2012, 8 pages.
U.S. Appl. No. 13/680,934, filed Nov. 19, 2012 Non-Final Office Action mailed Oct. 2, 2013, 7 pages.
U.S. Appl. No. 13/680,934, filed Nov. 19, 2012 Final Office Action mailed Feb. 10, 2014, 13 pages.
U.S. Appl. No. 13/680,934, filed Nov. 19, 2012 Notice of Allowance mailed Apr. 30, 2014, 9 pages.
U.S. Appl. No. 13/680,934, filed Nov. 19, 2012 Notice of Allowance mailed Jul. 25, 2014, 12 pages.
U.S. Appl. No. 13/886,873, filed May 3, 2013, Notice of Allowance mailed Oct. 24, 2014, 40 pages.
U.S. Appl. No. 13/919,702, filed Jun. 17, 2013 Non Final Office Action mailed Jun. 11, 2014, 25 pages.
U.S. Appl. No. 13/942,451, filed Jul. 15, 2013 Non Final Office Action mailed Jul. 28, 2014, 27 pages.
U.S. Appl. No. 13/971,579, filed Aug. 20, 2013 Non Final Office Action mailed Oct. 28, 2014, 35 pages.
U.S. Appl. No. 14/200,864, filed Mar. 7, 2014, Non-Final Office Action mailed Dec. 5, 2014, 35 pages.
Office Action for EP 14160140.1 mailed Jan. 19, 2016, 5 pages.
International Search Report and Written Opinion for PCT/EP2015/073299 mailed Jan. 4, 2016, 12 pages.
International Search Report and Written Opinion for PCT/EP2015/073936 mailed Feb. 4, 2016, all pages.
International Search Report and Written Opinion for PCT/GB2015/052570 mailed Dec. 11, 2015, 13 pages.
U.S. Appl. No. 14/485,188, filed Sep. 12, 2014, Final Rejection mailed Feb. 23, 2016, 22 pages.
U.S. Appl. No. 14/567,348, filed Dec. 11, 2014, Preinterview first office action mailed Jan. 20, 2016, 23 pages.
U.S. Appl. No. 14/470,248, filed Aug. 27, 2014, Final Office Action mailed Feb. 16, 2016, 26 pages.
U.S. Appl. No. 14/470,279, filed Aug. 27, 2014, Final Office Action mailed Jan. 22, 2016, 25 pages.
U.S. Appl. No. 14/479,007, filed Sep. 5, 2014, Final Office Action mailed Feb. 22, 2016, 37 pages.
U.S. Appl. No. 14/591,474, filed Jan. 7, 2015, Non-Final Office Action mailed Feb. 12, 2016, 32 pages.
U.S. Appl. No. 14/494,079, filed Sep. 23, 2014, Preinterview first office action mailed Feb. 10, 2016, 6 pages.
Fong A.C.M. et al, "Indoor air quality control for asthma patients using smart home technology," Consumer Electronics (ISCE), 2011 IEEE 15th International Symposium On, IEEE, Jun. 14, 2011, pp. 18-19, XP032007803, DOI: 10.1109/ISCE.2011.5973774, ISBN: 978-1-61284-843-3, Abstract and sections 3 and 4.
Shunfeng Cheng et al., "A Wireless Sensor System for Prognostics and Health Management," IEEE Sensors Journal, IEEE Service Center, New York, NY, US, vol. 10, No. 4, Apr. 1, 2010, pp. 856-862, XP011304455, ISSN: 1530-437X, Sections 2 and 3.
International Search Report and Written Opinion for PCT/EP2015/070286 mailed Nov. 5, 2015, 13 pages.
International Search Report and Written Opinion for PCT/GB2015/052544 mailed Nov. 6, 2015, 10 pages.
International Search Report and Written Opinion for PCT/EP2015/069461 mailed Oct. 1, 2015, 13 pages.
International Search Report and Written Opinion for PCT/EP2015/069456 mailed Oct. 5, 2015, all pages.
International Preliminary Report on Patentability for PCT/US2014/033796 issued Nov. 3, 2015, all pages.
International Search Report and Written Opinion for PCT/EP2015/069681 mailed Nov. 23, 2015, all pages.
International Search Report and Written Opinion for PCT/GB2015/052457 mailed Nov. 13, 2015, 11 pages.
U.S. Appl. No. 12/700,310, filed Feb. 4, 2010 Final Office Action mailed Oct. 26, 2015, 19 pages.
U.S. Appl. No. 14/107,132, filed Dec. 16, 2013, Final Rejection mailed Dec. 16, 2015, 32 pages.
U.S. Appl. No. 14/071,613, filed Nov. 4, 2013 Final Office Action mailed Oct. 8, 2015, 11 pages.
U.S. Appl. No. 14/470,392, filed Aug. 27, 2014 Non Final Office Action mailed Nov. 5, 2015, 31 pages.
U.S. Appl. No. 14/470,415, filed Aug. 27, 2014 Non Final Office Action mailed Nov. 18, 2015, 28 pages.
U.S. Appl. No. 13/942,451, filed Jul. 15, 2013 Non Final Office Action mailed Jan. 8, 2016, 41 pages.
U.S. Appl. No. 13/919,702, filed Jun. 17, 2013 Final Office Action mailed Dec. 31, 2015, 30 pages.
International Search Report and Written Opinion for PCT/US2016/028126 mailed Jun. 3, 2016, all pages.
U.S. Appl. No. 12/700,310, filed Feb. 4, 2010 Non-Final Office Action mailed Jun. 16, 2016, 30 pages.
U.S. Appl. No. 14/485,188, filed Sep. 12, 2014, Non-Final Rejection mailed Jun. 17, 2016, 29 pages.
U.S. Appl. No. 14/567,765, filed Dec. 11, 2014, Preinterview first office action mailed Apr. 8, 2016, 30 pages.
U.S. Appl. No. 14/577,717, filed Dec. 19, 2014, Preinterview first office action mailed Apr. 4, 2016, 29 pages.
U.S. Appl. No. 14/584,075, filed Dec. 29, 2014, Non-Final Rejection mailed Apr. 1, 2016, 40 pages.
U.S. Appl. No. 14/710,331, filed May 12, 2015, Non-Final Rejection mailed May 20, 2016, 42 pages.
U.S. Appl. No. 14/200,864, filed Mar. 7, 2014 Non-Final Office Action mailed Feb. 18, 2016, 61 pages.
U.S. Appl. No. 14/139,299, filed Dec. 23, 2013, Final Office Action mailed Feb. 25, 2016, all pages.
U.S. Appl. No. 14/139,420, filed Dec. 23, 2013 Notice of Allowance mailed Mar. 31, 2016, 37 pages.
U.S. Appl. No. 14/470,392, filed Aug. 27, 2014 Final Office Action mailed Mar. 4, 2016, all pages.
U.S. Appl. No. 14/470,415, filed Aug. 27, 2014 Final Office Action mailed Mar. 3, 2016, all pages.
International Preliminary Report on Patentability for PCT/US2014/053876 issued Jun. 14, 2016, 7 pages.
International Preliminary Report on Patentability for PCT/US2014/055441 issued Jun. 14, 2016, 8 pages.
International Search Report and Written Opinion for PCT/GB2015/052456 mailed Jun. 13, 2016, all pages.
International Preliminary Report on Patentability for PCT/US2014/055476 issued Jun. 14, 2016, 9 pages.
U.S. Appl. No. 14/528,739, filed Oct. 30, 2014 Notice of Allowance mailed Jun. 23, 2016, 34 pages.
U.S. Appl. No. 14/107,132, filed Dec. 16, 2013, Non Final Office Action mailed Jul. 18, 2016, all pages.
U.S. Appl. No. 14/715,248, filed May 18, 2015, Non-Final Rejection mailed Jul. 19, 2016, 34 pages.
U.S. Appl. No. 14/567,783, filed Dec. 11, 2014, Non Final Rejection mailed Aug. 23, 2016, all pages.
U.S. Appl. No. 14/470,248, filed Aug. 27, 2014, Non Final Office Action mailed Jul. 25, 2016, all pages.
U.S. Appl. No. 14/470,279, filed Aug. 27, 2014, Non Final Office Action mailed Jul. 19, 2016, all pages.
U.S. Appl. No. 14/479,007, filed Sep. 5, 2014, Non-Final Office Action mailed Jul. 27, 2016, 37 pages.

(56) References Cited

OTHER PUBLICATIONS

U.S. Appl. No. 13/942,451, filed Jul. 15, 2013 Final Office Action mailed Jun. 22, 2016, all pages.
U.S. Appl. No. 13/919,702, filed Jun. 17, 2013 Non Final Office Action mailed Jun. 30, 2016, all pages.
U.S. Appl. No. 14/139,299, filed Dec. 23, 2013, Non Final Office Action mailed Jun. 20, 2016, all pages.
U.S. Appl. No. 14/470,392, filed Aug. 27, 2014 Non-Final Office Action mailed Aug. 5, 2016, all pages.
U.S. Appl. No. 14/470,415, filed Aug. 27, 2014 Non Final Office Action mailed Jul. 29, 2016, all pages.
Office Action for EP14868928.4 dated Sep. 23, 2016, all pages.
U.S. Appl. No. 12/700,310, filed Feb. 4, 2010 Notice of Allowance mailed Nov. 8, 2016, all pages.
U.S. Appl. No. 14/567,765, filed Dec. 11, 2014, First Action interview mailed Oct. 18, 2016, all pages.
U.S. Appl. No. 14/584,075, filed Dec. 29, 2014, Final Rejection mailed Oct. 6, 2016, all pages.
U.S. Appl. No. 14/566,977, filed Dec. 11, 2014, Non Final Rejection mailed Oct. 3, 2016, all pages.
U.S. Appl. No. 14/567,754, filed Dec. 11, 2014, Non Final Rejection mailed Nov. 4, 2016, all pages.
U.S. Appl. No. 14/567,770, filed Dec. 11, 2014, Non Final Rejection mailed Nov. 4, 2016, all pages.
U.S. Appl. No. 14/671,299, filed Mar. 27, 2015, Non Final Rejection mailed Oct. 28, 2016, all pages.
U.S. Appl. No. 14/476,377, filed Sep. 3, 2014, Non-Final Rejection mailed Nov. 7, 2016, all pages.
U.S. Appl. No. 14/200,864, filed Mar. 7, 2014 Notice of Allowance mailed Sep. 15, 2016, all pages.
U.S. Appl. No. 15/195,527, filed Jun. 28, 2016, Non-Final Rejection mailed Sep. 30, 2016, all pages.
U.S. Appl. No. 13/942,451, filed Jul. 15, 2013 Non Final Office Action mailed Oct. 25, 2016, all pages.

* cited by examiner

IN-RESIDENCE TRACK AND ALERT

BACKGROUND

The advent of the digital video recorder, multi-tuner television receiver, and the availability of high-capacity and affordable computer-readable storage devices have made available many possibilities to television programming service providers and viewers alike. In addition, viewers have come to expect flexibility and convenience with respect to incorporating their television receivers into a home network computing environment.

SUMMARY

In an aspect, a method may include or comprise: detecting, by a television receiver, an in-bound telephone call; determining, by the television receiver, whether a calling party is authorized to access a message that provides an indication to the status of an individual as derived by the television receiver based upon a number of sensors positioned with a residence in which the television receiver serves as a gateway of a home automation system; and playing-back, by the television receiver for the calling party, the message that provides the indication to the status of the individual when the calling party is authorized to access the message.

In an aspect, a television receiver may include or comprise at least one processor, and at least one memory element communicatively coupled with and readable by at least one processor and having stored therein processor-readable instructions. The processor-readable instructions when executed by the at least one processor may cause the at least one processor to: detect an in-bound telephone call; determine whether a calling party is authorized to access a message that provides an indication to the status of an individual as derived by the television receiver based upon a number of sensors positioned with a residence in which the television receiver serves as a gateway of a home automation system; and play-back for the calling party the message that provides the indication to the status of the individual when the calling party is authorized to access the message.

In an aspect, a method may include or comprise: detecting, by a television receiver, an in-bound telephone call; analyzing, by the television receiver, a telephone number associated with the in-bound telephone call as a primary security measure to determine whether the calling party is authorized to access a message that provides an indication to the status of an individual as derived by the television receiver based upon a number of sensors positioned with a residence in which the television receiver serves as a gateway of a home automation system; authenticating, by the television receiver, the telephone number to determine that the calling party is authorized to access a secondary security measure to determine whether the calling party is authorized to access a message; analyzing, by the television receiver, a passcode entered by the calling party as the secondary security measure to determine whether the calling party is authorized to access the message; authenticating, by the television receiver, the passcode to determine that the calling party is authorized to access the message; and playing-back, by the television receiver for the calling party, the message that provides the indication to the status of the individual when the calling party is authorized to access the message. Other aspects are possible.

DETAILED DESCRIPTION

Figure 1:
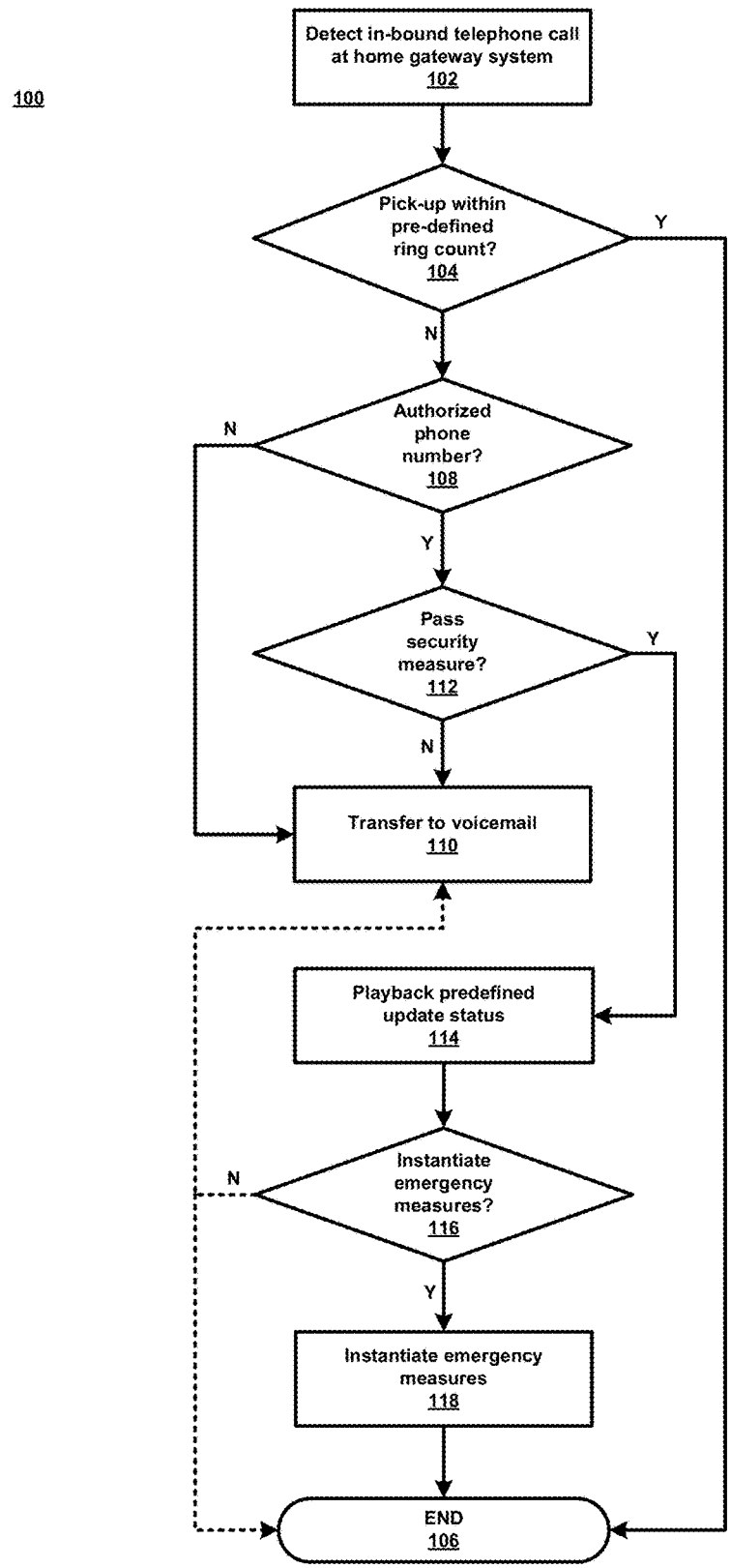
FIG. 1 shows a first example method according to the disclosure.

The present disclosure is generally directed to or towards systems and methods for monitoring, via a network of sensors each communicatively coupled to a home gateway system, movement and location of one or more individuals within their own residence. Here, it is contemplated that the system may also respond to inquiries as to a potential or probable or possible status of the one or more individuals within the residence. For example, the system may exhibit any particular combination of special-purpose firmware, software, and/or hardware, to enable the system to accept and process signals from a telephony system, that of which may be considered an originating source of the inquiry, and also to enable an inquiring individual or calling party to interact with the system in order to investigate the status of the one or more individuals within the residence. It is further contemplated that the various features or aspects of the present disclosure may be incorporated into or within a television receiver as part of a satellite television implementation. This may, among other things, serve to entice new customers to subscribe to services as offered by a particular satellite television provider, as well as provide an incentive for existing customers to maintain their loyalty and/or relationship with the particular satellite television provider. Although not so limited, an appreciation of the various aspects of the present disclosure may be gained from the following discussion in connection with the drawings. For instance, referring now to FIG. 1, a first example method 100 is shown in accordance with the present disclosure.

At step 102, a home gateway may detect an in-bound telephone call at a particular residence. Here, the home gateway may exhibit any particular combination of special-purpose firmware, software, and/or hardware, to enable the same to accept and process telephony signals, and also to enable a calling party to interact with the home gateway in order to investigate the status of a particular individual within the residence. Although not so limited, the home gateway may comprise a television receiver that, in addition to providing access to various satellite broadcast programming, may be configured and/or arranged to serve as the central controller and access point in a home network and home automation environment within the residence.

Accordingly, it is contemplated that the television receiver may be configured and/or arranged to discover and also establish a communication link to or with any of a plurality of so-called "smart devices," such as network printers, handheld mobile devices, and etc. Additionally, it is contemplated that the television receiver may be configured and/or arranged to discover and also establish a communication link to or with any of a plurality of sensor devices each one of which may be strategically positioned with the residence, such as sensors coupled to one or more HVAC (Heating, Ventilation, and Air-Conditioning) systems, sensors coupled to one or more audio-visual systems, sensors coupled to one or more shading (e.g., blinds/curtains) systems, sensors coupled to one or more security systems, sensors coupled to one or more household furnishings or appliances, and etc.

Next, at step 104, the home gateway may monitor telephone "ring-count" to determine whether or not the in-bound telephone call is or has been answered within a pre-determined and user-configurable number of rings or time period. For instance, the home gateway may monitor telephone ring-count in order to determine whether or not the in-bound telephone call is or has been answered within five (5) rings, for example. Alternatively, the home gateway may monitor status of the in-bound telephone call in order to determine whether or not the telephone call has been answered within three (3) minutes, for example. When, for instance, the home gateway determines that the in-bound telephone call has been answered within the pre-determined and user-configurable number of rings or time period, process flow may branch to termination step 106. When, however, the home gateway determines that the in-bound telephone call has not been answered within the pre-determined and user-configurable number of rings or time period, process flow may branch to step 108.

At step 108, the home gateway may make an initial determination as to whether or not the calling party is authorized to access and interact with the home gateway in order to investigate the status of the particular individual within the residence. For example, the home gateway may derive the telephone number of the calling party from the call itself, in a manner similar to that may performed in a "Caller ID" implementation, for instance. When, for example, the home gateway makes an initial determination that the calling party is not authorized to access and interact with the home gateway, process flow may branch to step 110. At step 110, the calling party may be transferred directly to voicemail, as managed and/or implemented by the home gateway in accordance with the principles of the present disclosure.

When, however, the home gateway makes an initial determination that the calling party is not authorized to access and interact with the home gateway, process flow may branch to step 112. At step 112, the calling party may be prompted by the home gateway to enter an authentication code, as a security measure so as to prevent unauthorized access to the home gateway. For example, the calling party may be prompted to enter an alphanumeric sequence such as a PIN (Personal Identification Number) number, or the like, into their telephone in order to gain access to the home gateway. When, for example, the home gateway makes a determination that an incorrect authentication code has been submitted, process flow may branch to step 110, where the calling party may be transferred directly voicemail. In some implementations, the calling party may be afforded the opportunity to "try again" once or maybe twice more before being transferred to voicemail.

When, however, the home gateway makes a determination that a correct authentication code has been submitted, process flow may branch to step 114. At step 114, the home gateway may playback a message that provides an indication to the calling party as to a "potential" or "probable" or "possible" status of the particular individual within the residence. Here, it is contemplated that the status might not be known to a certainty unless, for example, particular sensors (e.g., video cameras, infrared sensors, weight sensors, etc.) are employed that may be utilized to determine for a certainly location or status of the particular individual within the residence. In the present example though, assume that the calling party is the adult child of an aging parent, and that the adult child has preconfigured the home gateway to derive and consolidate the following information for insertion into the message: probable location within the residence; and appliances currently in an "on" state. In this example, it is contemplated that the home gateway may access a table or database or the like and then generate a message as follows: NAME is currently in the living room or adjacent dining room; and the dryer and the oven is currently in an "on" state. Here, the calling party may, based upon the content of the message, make a determination as to whether or not a possible emergency exists. Accordingly, it is contemplated that an option may be presented to the calling party to address a possible emergency situation.

For example, immediately following playback of the message (step 114), at step 116 the calling party may be prompted by the home gateway to enter a first particular code to provoke an emergency response, if it determined by the calling party that an emergency response needed or necessary in light of content of the playback message, or to enter a second particular code to bypass the option to initiate an emergency response altogether. When, for example, the home gateway determines that the second particular code has been entered by the calling party, the calling party may be prompted by the home gateway to make a selection to either terminate the call or be transferred to voicemail. Accordingly, in this scenario, process flow may branch to either step 110 or to termination step 106, indicated by intermittent line in FIG. 1, based upon the wishes of the calling party.

When, however, the home gateway determines that the first particular code has been entered by the calling party, process flow may branch to step 118 where one or more predefined and user-configurable emergency measures may be implemented or otherwise instantiated by the home gateway itself. Example emergency measures may include: dial 911; send text message to neighbor and/or relatives; disable or turn "off" appliances currently in the "on" state; and etc. In this manner, the calling party may interact with the home gateway to initially come to an understanding of the status of the particular individual within the residence, and then instantiate if found needed or necessary one or more measures to address a possible emergency situation. Process flow may then proceed to termination step 106. Further scenarios and/or beneficial aspects associated with monitoring, via a network of sensors each communicatively coupled to a home gateway system, movement and location of one or more individuals within their own residence are described in detail below in connection with FIGS. 2-8.

Figure 2:
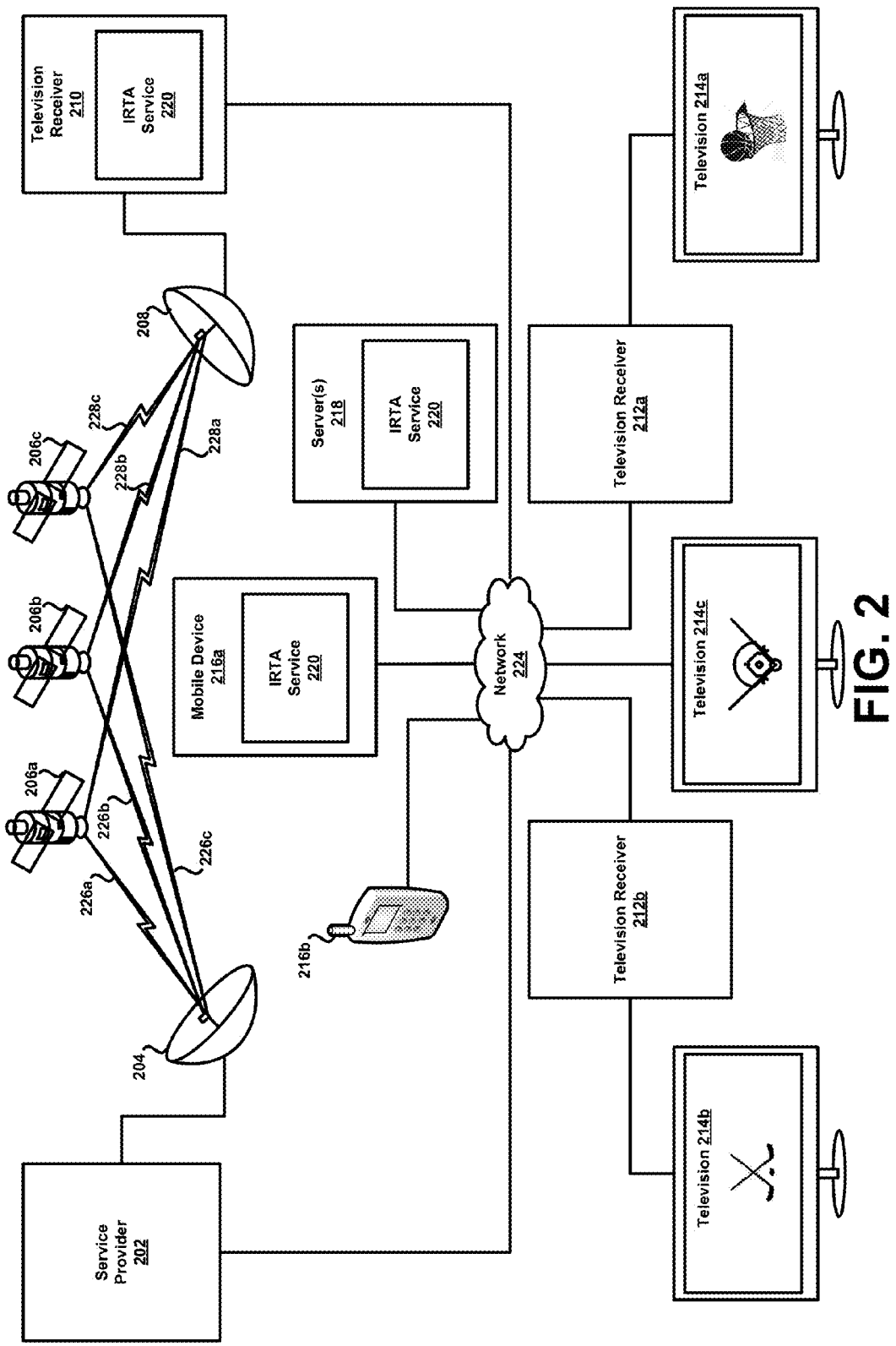
FIG. 2 shows an example content distribution system according to the disclosure.

Referring now to FIG. 2, an example satellite television distribution system 200 is shown in accordance with the present disclosure. For brevity, the system 200 is depicted in a simplified form, and may include more or fewer systems, devices, networks, and/or other components as desired. Further, number and type of features or elements incorporated within the system 200 may or may not be implementation-specific, and at least some of the aspects of the system 200 may be similar to a cable television distribution system, an IPTV (Internet Protocol Television) content distribution system, and/or any other type of content distribution system.

The example system 200 may include a service provider 202, a satellite uplink 204, a plurality of satellites 206a-c, a satellite dish 208, a PTR (Primary Television Receiver) 210, a plurality of STRs (Secondary Television Receivers) 212a-b, a plurality of televisions 214a-c, a plurality of computing devices 216a-b, and at least one server 218 that may be associated with the service provider 202. Additionally, the PTR 210, computing devices 216a-b, and the server 218 may include or otherwise exhibit an IRTA (In-Residence Track and Alert) service 220. In general, the IRTA service 220 may be configured and/or arranged to implement various features or aspects of the present disclose associated with monitoring, via a network of sensors each communicatively coupled to a home gateway system, the movement and location of one or more individuals within their own residence, and also associated with responding to inquiries as to a potential or probable or possible status of the one or more individuals within the residence. Such features may be beneficial and/or advantageous in many respects, and an appreciation of such benefits and/or advantages may be understood in light of the present disclosure in its entirety.

The system 200 may further include at least one network 224 that establishes a bidirectional communication path for data transfer between and among each respective element of the system 200, outside or separate from the unidirectional satellite signaling path. The network 224 is intended to represent any number of terrestrial and/or non-terrestrial network features or elements. For example, the network 224 may incorporate or exhibit any number of features or elements of various wireless and/or hardwired packet-based communication networks such as, for example, a WAN (Wide Area Network) network, a HAN (Home Area Network) network, a LAN (Local Area Network) network, a WLAN (Wireless Local Area Network) network, the Internet, a cellular communications network, or any other type of communication network configured such that data may be transferred between and among respective elements of the system 200.

The PTR 210, and the STRs 212a-b, as described throughout may generally be any type of television receiver, television converter, etc., such as a STB for example. In another example, the PTR 210, and the STRs 212a-b, may exhibit functionality integrated as part of or into a television, a DVR (Digital Video Recorder), a computer such as a tablet computing device, or any other computing system or device, as well as variations thereof. Further, the PTR 210 and the network 224, together with the STRs 212a-b and televisions 214a-c, and possibly the computing devices 216a-b, may each be incorporated within or form at least a portion of a particular home computing network. Further, the PTR 210 may be configured so as to enable communications in accordance with any particular communication protocol(s) and/or standard(s) including, for example, TCP/IP (Transmission Control Protocol/Internet Protocol), DLNA/DTCP-IP (Digital Living Network Alliance/Digital Transmission Copy Protection over Internet Protocol), HDMI/HDCP (High-Definition Multimedia Interface/High-bandwidth Digital Content Protection), etc. Other examples are possible. For example, one or more of the various elements or components of the example system 200 may be configured to communicate in accordance with the MoCA® (Multimedia over Coax Alliance) home entertainment networking standard. Still other examples are possible.

In practice, the satellites 206a-c may each be configured to receive uplink signals 226a-c from the satellite uplink 204. In this example, each the uplink signals 226a-c may contain one or more transponder streams of particular data or content, such as one or more particular television channels, as supplied by the service provider 202. For example, each of the respective uplink signals 226a-c may contain various media or media content such as encoded HD (High Definition) television channels, SD (Standard Definition) television channels, on-demand programming, programming information, and/or any other content in the form of at least one transponder stream, and in accordance with an allotted carrier frequency and bandwidth. In this example, different media content may be carried using different ones of the satellites 206a-c.

Further, different media content may be carried using different transponders of a particular satellite (e.g., satellite 206a); thus, such media content may be transmitted at different frequencies and/or different frequency ranges. For example, a first and second television channel may be carried on a first carrier frequency over a first transponder of satellite 206a, and a third, fourth, and fifth television channel may be carried on second carrier frequency over a first transponder of satellite 206b, or, the third, fourth, and fifth television channel may be carried on a second carrier frequency over a second transponder of satellite 206a, and etc. Each of these television channels may be scrambled such that unauthorized persons are prevented from accessing the television channels.

The satellites 206a-c may further be configured to relay the uplink signals 226a-c to the satellite dish 208 as downlink signals 228a-c. Similar to the uplink signals 226a-c, each of the downlink signals 228a-c may contain one or more transponder streams of particular data or content, such as various encoded and/or at least partially electronically scrambled television channels, on-demand programming, etc., in accordance with an allotted carrier frequency and bandwidth. The downlink signals 228a-c, however, may not necessarily contain the same or similar content as a corresponding one of the uplink signals 226a-c. For example, the uplink signal 226a may include a first transponder stream containing at least a first group or grouping of television channels, and the downlink signal 228a may include a second transponder stream containing at least a second, different group or grouping of television channels. In other examples, the first and second group of television channels may have one or more television channels in common. In sum, there may be varying degrees of correlation between the uplink signals 226a-c and the downlink signals 228a-c, both in terms of content and underlying characteristics.

Further, satellite television signals may be different from broadcast television or other types of signals. Satellite signals may include multiplexed, packetized, and modulated digital signals. Once multiplexed, packetized and modulated, one analog satellite transmission may carry digital data representing several television stations or service providers. Some examples of service providers include HBO®, CBS®, ESPN®, and etc. Further, the term "channel," may in some contexts carry a different meaning from or than its normal plain language meaning. For example, the term "channel" may denote a particular carrier frequency or sub-band which can be tuned to by a particular tuner of a television receiver. In other contexts though, the term "channel" may refer to a single program/content service such as HBO®.

Additionally, a single satellite may typically have multiple transponders (e.g., 32 transponders) each one broadcasting a channel or frequency band of about 24-27 MHz in a broader frequency or polarity band of about 500 MHz.

Thus, a frequency band of about 500 MHz may contain numerous sub-bands or channels of about 24-27 MHz, and each channel in turn may carry a combined stream of digital data comprising a number of content services. For example, a particular hypothetical transponder may carry HBO®, CBS®, ESPN®, plus several other channels, while another particular hypothetical transponder may itself carry 3, 4, 5, 6, etc., different channels depending on the bandwidth of the particular transponder and the amount of that bandwidth occupied by any particular channel or service on that transponder stream. Further, in many instances a single satellite may broadcast two orthogonal polarity bands of about 500 MHz. For example, a first polarity band of about 500 MHz broadcast by a particular satellite may be left-hand circular polarized, and a second polarity band of about 500 MHz may be right-hand circular polarized. Other examples are possible.

Continuing with the example scenario, the satellite dish 208 may be provided for use to receive television channels (e.g., on a subscription basis) provided by the service provider 202, satellite uplink 204, and/or satellites 206a-c. For example, the satellite dish 208 may be configured to receive particular transponder streams, or downlink signals 228a-c, from one or more of the satellites 206a-c. Based on the characteristics of the PTR 210 and/or satellite dish 208, however, it may only be possible to capture transponder streams from a limited number of transponders concurrently. For example, a particular tuner of the PTR 210 may be configured to tune to a single transponder stream from a transponder of a single satellite at a time.

Additionally, the PTR 210, which is communicatively coupled to the satellite dish 208, may subsequently select via tuner, decode, and relay particular transponder streams to the television 214c for display thereon. For example, the satellite dish 208 and the PTR 210 may, respectively, be configured to receive, decode, and relay at least one premium HD-formatted television channel to the television 214c. Programming or content associated with the HD channel may generally be presented live, or from a recording as previously stored on, by, or at the PTR 210. Here, the HD channel may be output to the television 214c in accordance with the HDMI/HDCP content protection technologies. Other examples are however possible.

Further, the PTR 210 may select via tuner, decode, and relay particular transponder streams to one or both of the STRs 212a-b, which may in turn relay particular transponder streams to a corresponding one of the televisions 214a-b for display thereon. For example, the satellite dish 208 and the PTR 210 may, respectively, be configured to receive, decode, and relay at least one television channel to the television 214a by way of the STR 212a. Similar to the above-example, the television channel may generally be presented live, or from a recording as previously stored on the PTR 210, and may be output to the television 214a by way of the STR 212a in accordance with a particular content protection technology and/or networking standard. Still further, the satellite dish 208 and the PTR 210 may, respectively, be configured to receive, decode, and relay at least one premium television channel to one or each of the computing devices 216a-c. Similar to the above-examples, the television channel may generally be presented live, or from a recording as previously stored on the PTR 210, and may be output to one or both of the computing devices 216a-c in accordance with a particular content protection technology and/or networking standard.

Figure 3:
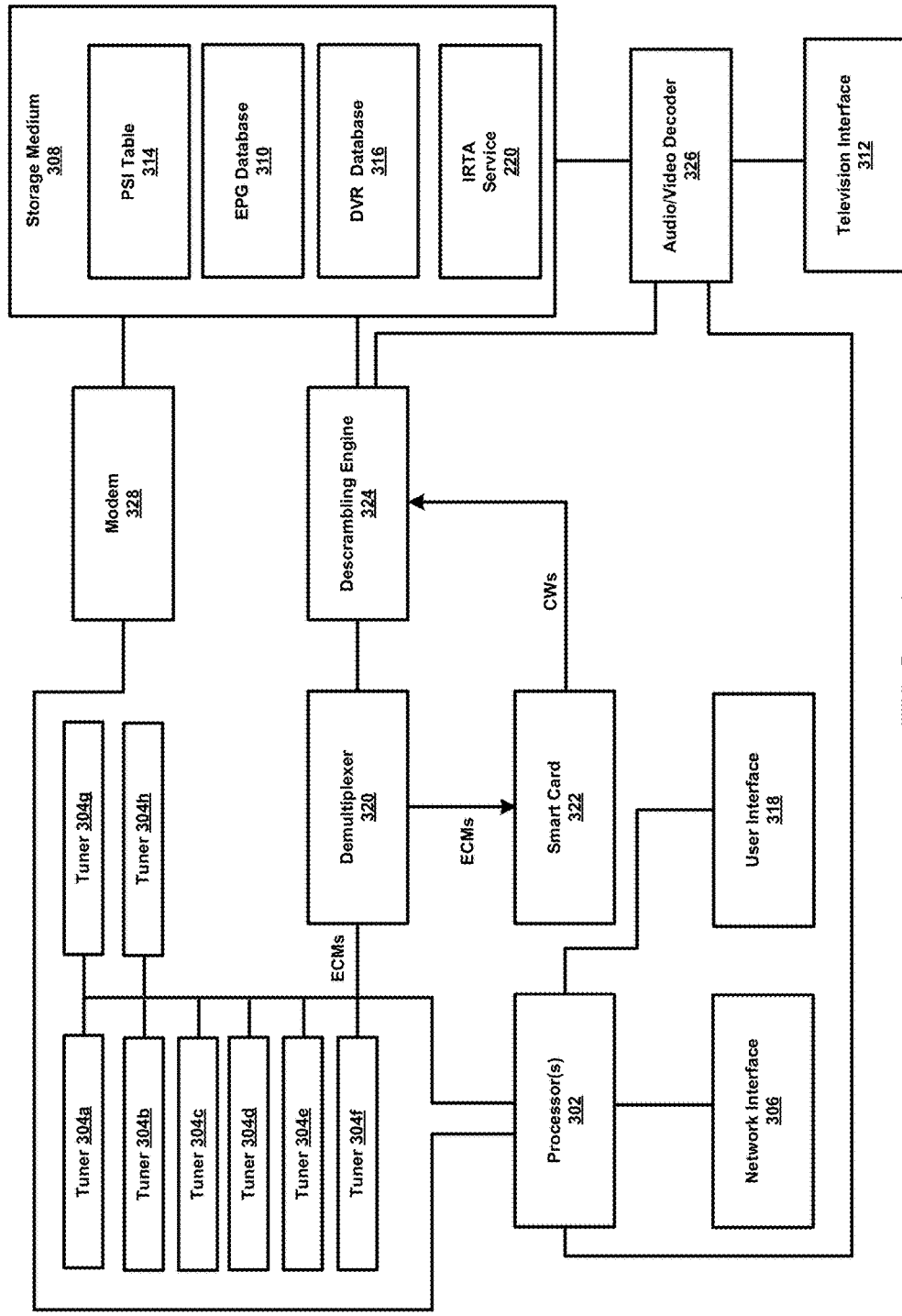
FIG. 3 shows an example block diagram of a television receiver of FIG. 2.

Referring now to FIG. 3, an example block diagram of the PTR 210 of FIG. 2 is shown in accordance with the disclosure. In some examples, the STRs 312a-b may be configured in a manner similar to that of the PTR 210. In some examples, the STRs 312a-b may be configured and arranged to exhibit a reduced functionality as compared to the PTR 210, and may depend at least to a certain degree on the PTR 210 to implement certain features or functionality. The STRs 312a-b in this example may be each referred to as a "thin client."

The PTR 210 may include one or more processors 302, a plurality of tuners 304a-h, at least one network interface 306, at least one non-transitory computer-readable storage medium 308, at least one EPG (Electronic Programming Guide) database 310, at least one television interface 312, at least one PSI (Program Specific Information) table 314, at least one DVR database 316, at least one user interface 318, at least one demultiplexer 320, at least one smart card 322, at least one descrambling engine 324, at least one decoder 326, and at least one modem 328. In other examples, fewer or greater numbers of components may be present. Further, functionality of one or more components may be combined; for example, functions of the descrambling engine 324 may be performed by the processors 302. Still further, functionality of components may be distributed among additional components, and possibly additional systems such as, for example, in a cloud-computing implementation.

The processors 302 may include one or more specialized and/or general-purpose processors configured to perform processes such as tuning to a particular channel, accessing and displaying EPG information, and/or receiving and processing input from a user. For example, the processors 302 may include one or more processors dedicated to decoding video signals from a particular format, such as according to a particular MPEG (Motion Picture Experts Group) standard, for output and display on a television, and for performing or at least facilitating decryption or descrambling.

The tuners 304a-h may be used to tune to television channels, such as television channels transmitted via satellites 306a-c. Each one of the tuners 304a-h may be capable of receiving and processing a single stream of data from a satellite transponder, or a cable RF channel, at a given time. As such, a single tuner may tune to a single transponder or, for a cable network, a single cable channel. Additionally, one tuner (e.g., tuner 304a) may be used to tune to a television channel on a first transponder stream for display using a television, while another tuner (e.g., tuner 304b) may be used to tune to a television channel on a second transponder for recording and viewing at some other time. If multiple television channels transmitted on the same transponder stream are desired, a particular tuner (e.g., tuner 304c) may be used to receive the signal containing the multiple television channels for presentation and/or recording of each of the respective multiple television channels, such as in a PTAT (Primetime Anytime) implementation for example. Although eight tuners are shown, the PTR 210 may include more or fewer tuners (e.g., three tuners, sixteen tuners, etc.), and the features of the disclosure may be implemented similarly and scale according to the number of tuners of the PTR 210.

The network interface 306 may be used to communicate via alternate communication channel(s) with a service provider. For example, the primary communication channel between the service provider 202 of FIG. 2 and the PTR 210 may be via satellites 306a-c, which may be unidirectional to the PTR 210, and an another communication channel between the service provider 202 and the PTR 210, which may be bidirectional, may be via the network 224. In general, various types of information may be transmitted and/or received via the network interface 306.

The storage medium 308 may represent a non-transitory computer-readable storage medium. The storage medium 308 may include memory and/or a hard drive. The storage medium 308 may be used to store information received from one or more satellites and/or information received via the network interface 306. For example, the storage medium 308 may store information related to the EPG database 310, the PSI table 314, and/or the DVR database 316, among other elements or features, such as the IRTA service 220 mentioned above. Recorded television programs may be stored using the storage medium 308 and ultimately accessed therefrom.

The EPG database 310 may store information related to television channels and the timing of programs appearing on such television channels. Information from the EPG database 310 may be used to inform users of what television channels or programs are available, popular and/or provide recommendations. Information from the EPG database 310 may be used to generate a visual interface displayed by a television that allows a user to browse and select television channels and/or television programs for viewing and/or recording. Information used to populate the EPG database 310 may be received via the network interface 306 and/or via satellites 206a-c of FIG. 2. For example, updates to the EPG database 310 may be received periodically or at least intermittently via satellite. The EPG database 310 may serve as an interface for a user to control DVR functions of the PTR 210, and/or to enable viewing and/or recording of multiple television channels simultaneously.

The decoder 326 may convert encoded video and audio into a format suitable for output to a display device. For instance, the decoder 326 may receive MPEG video and audio from the storage medium 308, or the descrambling engine 324, to be output to a television. MPEG video and audio from the storage medium 308 may have been recorded to the DVR database 316 as part of a previously-recorded television program. The decoder 326 may convert the MPEG video and audio into a format appropriate to be displayed by a television or other form of display device and audio into a format appropriate to be output from speakers, respectively. The decoder 326 may be a single hardware element capable of decoding a finite number of television channels at a given time, such as in a time-division arrangement. In the example embodiment, eight television channels may be decoded concurrently or simultaneously.

The television interface 312 output a signal to a television, or another form of display device, in a proper format for display of video and play back of audio. As such, the television interface 312 may output one or more television channels, stored television programming from the storage medium 308, such as television programs from the DVR database 316 and/or information from the EPG database 310 for example, to a television for presentation.

The PSI table 314 may store information used by the PTR 210 to access various television channels. Information used to populate the PSI table 314 may be received via satellite, or cable, through the tuners 304a-h and/or may be received via the network interface 306 over the network 224 from the service provider 202 shown in FIG. 2. Information present in the PSI table 314 may be periodically or at least intermittently updated. Information that may be present in the PSI table 314 may include: television channel numbers, satellite identifiers, frequency identifiers, transponder identifiers, ECM PIDs (Entitlement Control Message, Packet Identifier), one or more audio PIDs, and video PIDs. A second audio PID of a channel may correspond to a second audio program, such as in another language. In some examples, the PSI table 314 may be divided into a number of tables, such as a NIT (Network Information Table), a PAT (Program Association Table), and a PMT (Program Management Table).

Table 1 below provides a simplified example of the PSI table 314 for several television channels. It should be understood that in other examples, many more television channels may be represented in the PSI table 314. The PSI table 314 may be periodically or at least intermittently. As such, television channels may be reassigned to different satellites and/or transponders, and the PTR 210 may be able to handle this reassignment as long as the PSI table 314 is updated.

TABLE 1

| Channel | Satellite | Transponder | ECM PID | Audio PIDs | Video PID |
|---------|-----------|-------------|---------|------------|-----------|
| 4       | 1         | 2           | 27      | 2001       | 1011      |
| 5       | 2         | 11          | 29      | 2002       | 1012      |
| 7       | 2         | 3           | 31      | 2003       | 1013      |
| 13      | 2         | 4           | 33      | 2003, 2004 | 1013      |

It should be understood that the values provided in Table 1 are for example purposes only. Actual values, including how satellites and transponders are identified, may vary. Additional information may also be stored in the PSI table 314. Video and/or audio for different television channels on different transponders may have the same PIDs. Such television channels may be differentiated based on which satellite and/or transponder to which a tuner is tuned.

DVR functionality of the PTR 210 may permit a television channel to be recorded for a period of time. The DVR database 316 may store timers that are used by the processors 302 to determine when a television channel should be tuned to and recorded to the DVR database 245 of storage medium 308. In some examples, a limited amount of space of the storage medium 308 may be devoted to the DVR database 316. Timers may be set by the service provider 202 and/or one or more users of the PTR 210. DVR functionality of the PTR 210 may be configured by a user to record particular television programs. The PSI table 314 may be used by the PTR 210 to determine the satellite, transponder, ECM PID, audio PID, and video PID.

The user interface 318 may include a remote control, physically separate from PTR 210, and/or one or more buttons on the PTR 210 that allows a user to interact with the PTR 210. The user interface 318 may be used to select a television channel for viewing, view information from the EPG database 310, and/or program a timer stored to the DVR database 316 wherein the timer may be used to control the DVR functionality of the PTR 210.

Referring back to the tuners 304a-h, television channels received via satellite may contain at least some encrypted or scrambled data. Packets of audio and video may be scrambled to prevent unauthorized users, such as nonsubscribers, from receiving television programming without paying the service provider 202. When one of the tuners 304a-h is receiving data from a particular transponder of a satellite, the transponder stream may be a series of data packets corresponding to multiple television channels. Each data packet may contain a PID, which in combination with the PSI table 314, can be determined to be associated with a particular television channel. Particular data packets, referred to as ECMs may be periodically transmitted. ECMs may be encrypted; the PTR 210 may use the smart card 322 to decrypt ECMs.

The smart card 322 may function as the CA (Controlled Access) which performs decryption of encryption data to obtain control words that are used to descramble video and/or audio of television channels. Decryption of an ECM may only be possible when the user (e.g., an individual who is associated with the PTR 210) has authorization to access the particular television channel associated with the ECM. When an ECM is received by the demultiplexer 320 and the ECM is determined to correspond to a television channel being stored and/or displayed, the ECM may be provided to the smart card 322 for decryption.

When the smart card 322 receives an encrypted ECM from the demultiplexer 320, the smart card 322 may decrypt the ECM to obtain some number of control words. In some examples, from each ECM received by the smart card 322, two control words are obtained. In some examples, when the smart card 322 receives an ECM, it compares the ECM to the previously received ECM. If the two ECMs match, the second ECM is not decrypted because the same control words would be obtained. In other examples, each ECM received by the smart card 322 is decrypted; however, if a second ECM matches a first ECM, the outputted control words will match; thus, effectively, the second ECM does not affect the control words output by the smart card 322. When an ECM is received by the smart card 322, it may take a period of time for the ECM to be decrypted to obtain the control words. As such, a period of time, such as about 0.2-0.5 seconds, may elapse before the control words indicated by the ECM can be obtained. The smart card 322 may be permanently part of the PTR 210 or may be configured to be inserted and removed from the PTR 210.

The demultiplexer 320 may be configured to filter data packets based on PIDs. For example, if a transponder data stream includes multiple television channels, data packets corresponding to a television channel that are not desired to be stored or displayed by the user may be ignored by the demultiplexer 320. As such, only data packets corresponding to the one or more television channels desired to be stored and/or displayed may be passed to either the descrambling engine 324 or the smart card 322; other data packets may be ignored. For each channel, a stream of video packets, a stream of audio packets and/or a stream of ECM packets may be present, each stream identified by a PID. In some examples, a common ECM stream may be used for multiple television channels. Additional data packets corresponding to other information, such as updates to the PSI table 314, may be appropriately routed by the demultiplexer 320.

The descrambling engine 324 may use the control words output by the smart card 322 in order to descramble video and/or audio corresponding to television channels for storage and/or presentation. Video and/or audio data contained in the transponder data stream received by the tuners 304*a-h* may be scrambled. The video and/or audio may be descrambled by the descrambling engine 324 using a particular control word. Which control word output by the smart card 322 to be used for successful descrambling may be indicated by a scramble control identifier present within the data packet containing the scrambled video or audio. Descrambled video and/or audio may be output by the descrambling engine 324 to the storage medium 308 for storage, such as part of the DVR database 316 for example, and/or to the decoder 326 for output to a television or other presentation equipment via the television interface 312.

The modem 328 may be used by the PTR 210 as an interface between the digital data of the PTR 210 and the analog signal of a telephone line. It is contemplated that at least the modem 328 may enable the PTR 210 to implement various features and/or aspects associated with responding to inquiries as to a potential status of the one or more individuals within a residence as discussed within the context of the present disclosure.

For brevity, the PTR 210 is depicted in a simplified form, and may generally include more or fewer elements or components as desired, including those configured and/or arranged for implementing various features for controlling, based upon one or more predefined and user-configurable criterion, the loudness or intensity of audio as output by a particular computing device. For example, the PTR 210 is shown in FIG. 3 to include the IRTA service 220 as mentioned above in connection with FIG. 2. While shown stored to the storage medium 308 as executable instructions, the IRTA service 220 could, wholly or at least partially, be stored to the processor(s) 302 of the PTR 210. Further, some routing between the various modules of PTR 210 has been illustrated. Such illustrations are for exemplary purposes only. The state of two modules not being directly or indirectly connected does not indicate the modules cannot communicate. Rather, connections between modules of the PTR 210 are intended only to indicate possible common data routing. It should be understood that the modules of the PTR 210 may be combined into a fewer number of modules or divided into a greater number of modules.

Additionally, although not explicitly shown in FIG. 3, the PTR 210 may include one or more logical modules configured to implement a television steaming media functionality that encodes video into a particular format for transmission over the Internet such as to allow users to remotely view and control a home cable, satellite, or personal video recorder system from an Internet-enabled computer with a broadband Internet connection. The Slingbox® by Sling Media, Inc. of Foster City, Calif., is one example of a product that implements such functionality. Further, the PTR 210 may be configured to include any number of other various components or logical modules that are implemented in hardware, software, firmware, or any combination thereof, and such components or logical modules may or may not be implementation-specific.

Figure 4:
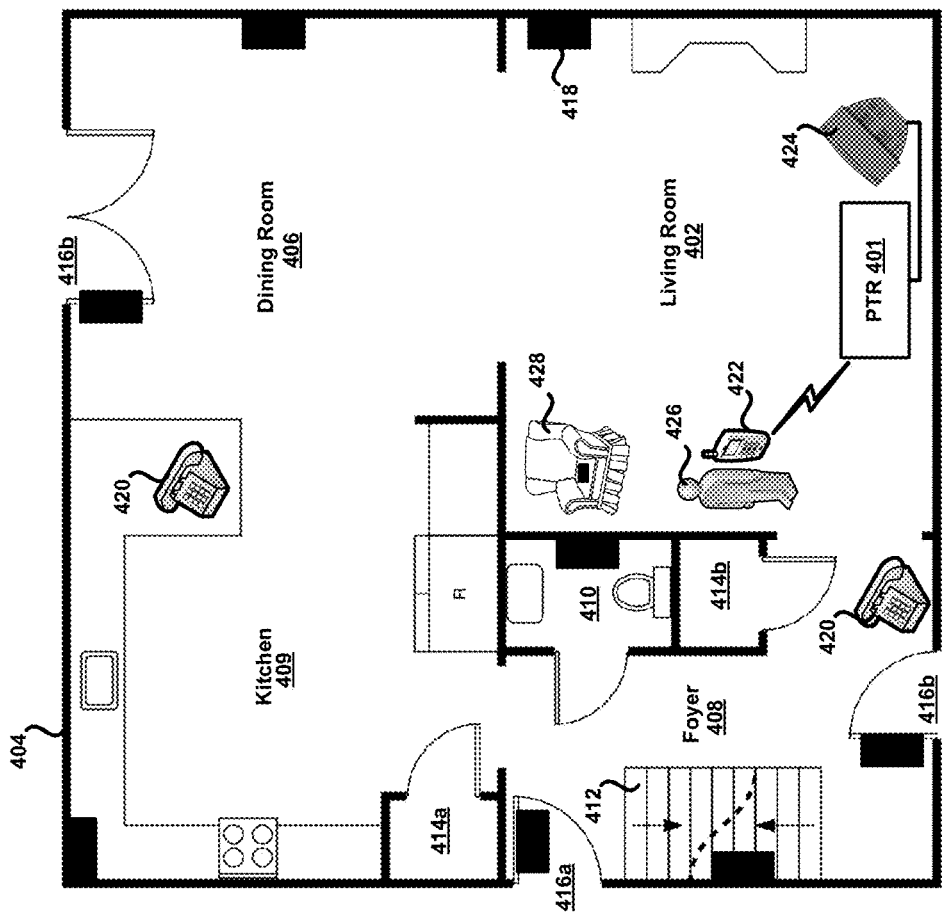
FIG. 4 shows first example aspects of the system of FIG. 2 in detail.

Referring now to FIG. 4, first example aspects of the system 200 of FIG. 2 are shown in detail. In particular, a PTR 401 that is configured and/or arranged in manner substantially similar to the PTR 210 of FIG. 2 is shown located or positioned within a living room 402 of a particular residence 404, and adjacent to the living room 402 is a dining room 406 and foyer 408. Also shown in FIG. 4 is a kitchen 409, a restroom 410, a stairwell 412, a number of closets 414*a-b*, and a number of doorways 416*a-c* that each lead from one particular area within the residence 404 to another particular area either within or out of the residence 404. Since the PTR 401 is configured and/or arranged in manner substantially similar to the PTR 210 of FIG. 2, it is contemplated that the PTR 401 may be, in addition to providing access to various satellite broadcast programming, configured and/or arranged to serve as the central controller and access point in a home network and home automation environment of the residence 404.

For example, various sensors 418, illustrated as "black boxes" in FIG. 4 for simplicity are shown positioned to a number of different locations within the residence 404. It is contemplated that each particular one of the sensors 418 could take the form of a particular type of sensor or like system or device, that which may not necessarily be the same as any other one or ones of the sensors 418. Examples of a particular type of sensor or like system or device may include: motion sensor; still camera; video camera; occupancy sensor; light sensor; temperature sensor; humidity sensor; infrared sensor; fire alarm sensor; carbon monoxide sensor; flood or leak sensor; proximity sensor; contact sensor; glass break sensor; audio sensor, and etc. Other types of sensors might be more specific or directed to a home automation implementation, such as: one or more sensors coupled to HVAC systems; one or more sensors coupled to audio-visual systems; one or more sensors coupled to shading systems; one or more sensors coupled to security systems; one or more sensors coupled to household furnishings or appliances; and etc. Additionally, although not explicitly shown in FIG. 4, it is contemplated that one or more sensors may be positioned external the residence 404. Examples of a particular type of sensor or like system or device that may be positioned external the residence 404 may include: driveway probes; lawn sprinkler sensor; garage door sensors; and etc.

In accordance with the present disclosure, each particular one of the sensors 418 as shown or described may be communicatively coupled to the PTR 401, along with landline telephones 420, a smartphone 422, and a television 424, such that a network of various computing systems, devices, etc., are each communicatively coupled to the PTR 401, of which may, individually or collectively, enable the PTR 401 to function as a home gateway in accordance with the present disclosure. Specifically, it is contemplated that the PTR 401 is a home gateway that is configured and/or arranged for monitoring the movement and location of at least one individual 426 within the residence 404, and also for responding to inquiries as to a potential or probable or possible status of the individual 426 within the residence 404. Here, it is contemplated that dedicated wiring (e.g., twisted pair, coaxial, HomePlug®, etc.) may be used or utilized to communicatively couple one or more of the sensors 418, and/or one or more of the telephones 420, and/or the smartphone 422, and/or the television 424 to the PTR 401. It is further contemplated that a wireless communication link (e.g., WiFi, Bluetooth®, cellular, etc.,) may be used or utilized to communicatively couple one or more of the sensors 418, and/or one or more of the telephones 420, and/or the smartphone 422, and/or the television 424 to the PTR 401.

Figure 5:
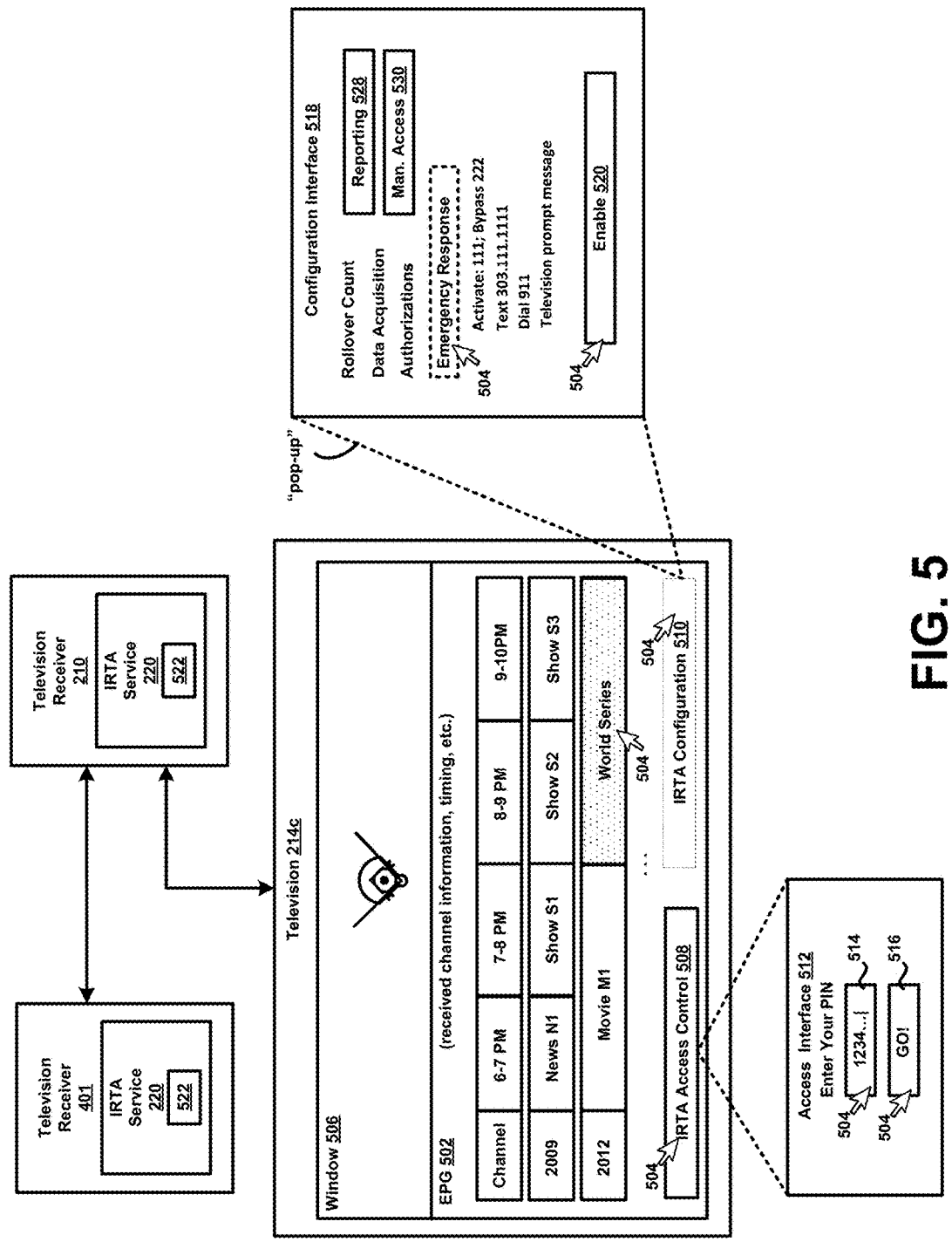
FIG. 5 shows second example aspects of the system of FIG. 2 in detail.

Referring now to FIG. 5, second example aspects of the system 200 of FIG. 2 are shown in detail. In particular, the PTR 210 may be configured to output an EPG (Electronic Programming Guide) 502 to and for presentation the television 214c, for example. The EPG 502 may at least present various information related to television channels and the timing of programs or programming appearing on such television channels. For example, as shown in FIG. 5, the EPG 502 may display information associated with a channel 2012, where the "World Series" is listed as scheduled to appear on that channel starting at a particular time on a particular day, and etc. In this example, and assuming that a current or instant time is sometime during the time period 8-10 PM, a viewer may manipulate a cursor 504 using a pointing device (not shown) to select, as indicated by stipple shading in FIG. 5, the World Series for immediate viewing within a window 506 on the television 214c. Other examples are possible. For example, it is contemplated that any menu-driven navigation technique or implementation may be used to enable user-interaction with the EPG 502, along with any other elements or interfaces output by the PTR 210 to the television 214c.

In addition to the EPG 502, the PTR 210 may be configured to output various other interactive elements or interfaces. For example, the IRTA service 220 of the PTR 210 may be configured to output a control selection 508 and a configuration selection 510 as shown in FIG. 5. In general, the control selection 508 may be considered an access control mechanism to prevent those who may not necessarily be authorized from accessing functionality associated with the configuration selection 510. Accordingly, in practice, the control selection 508 may be selected in order to gain access to a particular interface to configure a particular instance of the IRTA service 220 to function or otherwise operate in manner as desired. For example, a particular individual may manipulate the cursor 504 to select the control selection 508, via a "point and double-click" action, for example and, in response, the IRTA service 220 of the PTR 210 may output an access interface 512 to and for presentation by the television 214c. In this example, the access interface 512 may include a prompt "Enter Your PIN" along with a data field 514 and an enter selection 516. Here, the viewer may enter into the data field 514 an alphanumeric sequence, or the like, and then select the enter selection 516 in effort to gain access to functionality associated with the configuration selection 510.

Assuming that the above-mentioned alphanumeric sequence is authenticated by the IRTA service 220 of the PTR 210 following the described sequence, the configuration selection 510 may become "active" so that upon selection of the same a configuration interface 518 may be output to and for presentation by the television 214c. In FIG. 5, the configuration selection 510 is shown as "inactive," indicated by a perimeter line that is weighted less than that of the control selection 508, or by a perimeter line that is lighter in terms of boldness than that of the control selection 508. When the configuration selection 510 becomes "active," the perimeter line of the same would be similar to that of the control selection 508 as shown in FIG. 5.

Again, assuming that the alphanumeric sequence is authenticated by the IRTA service 220 of the PTR 210 following the described sequence, the viewer may manipulate the cursor 504 to select the configuration selection 510 and, in response, the IRTA service 220 of the PTR 210 may output the configuration interface 518 to and for presentation by the television 214c. Here, it is contemplated that the viewer may utilize the configuration interface 518 to configure the IRTA service 220 of another, different television receiver that is though configured and/or arranged the same as the PTR 210, such as the IRTA service 220 of the PTR 401 as shown in FIG. 5, so as to implement or otherwise enable one or more features or aspects of the present disclosure. Such an implementation may be beneficial and/or advantageous in many respects.

For example, assume that viewer in the example scenario is the adult child of an aging parent—the individual 426 within the residence 404 as discussed above in connection with FIG. 4. Here, the viewer may, from the comfort of their own home, program on behalf of the individual 426 the IRTA service 220 of the PTR 401 in a manner consistent with the principles of the present disclosure. Not only is this convenient for the viewer, to program and reprogram the IRTA service 220 of the PTR 401, it is also convenient and/or less burdensome for the individual 426, who might not necessarily be computer literate or even inclined or willing to program and reprogram the IRTA service 220 of the PTR 401. Other scenarios in which such an implementation may be beneficial and/or advantages may include situations in which the individual 426 is mentally and/or physically disabled, a law offender, a minor, and etc.

Returning to the configuration interface 518 of FIG. 5, the configuration interface 518 may include a number of fields to enable the viewer to define various parameters consistent with the principles of the present disclosure such as, for example, "Rollover Count" and "Data Acquisition" and "Authorizations" and "Emergency Response." The configuration interface 518 as shown in FIG. 5 is just an example. Other examples may include more or fewer "fields" as desired, and may be implementation-specific, and further may evolve as technology evolves.

In practice, and continuing with the example of FIG. 4 for convenience only, the Rollover Count field may be selected to highlight that field, or place that field in-focus, etc., to enable the viewer to define a "ring-count," or a number of times the telephone(s) 420 of FIG. 4 is permitted or allowed to ring before a rollover to the IRTA service 220 of the PTR 401, in a manner similar to that discussed above in connection with FIG. 1. Alternatively, the Rollover Count field may be selected to enable the viewer to define a time period the telephone(s) 420 of FIG. 4 is permitted or allowed to ring before a rollover to the IRTA service 220 of the PTR 401. In this manner, the particular individual may tailor or otherwise customize the parameter associated with the Rollover Count field. Such an implementation may be beneficial and/or advantageous in many respects. For example, it will be appreciated that the mobility of an elderly person may change over time, and the parameter associated with the Rollover Count field may be adjusted accordingly to account for this.

The Data Acquisition field may be selected to highlight that field, or place that field in-focus, to enable the viewer to define a frequency by which sensor data is acquired and served to the IRTA service 220 of the PTR 401. An example of such a definition may include "1 minute interval (e.g., periodic)" or "10 minute interval" and etc. In this manner, the viewer may tailor or otherwise customize the parameter associated with the Data Acquisition field. Such an implementation may be beneficial and/or advantageous in many respects. For example, system resources might be more intelligently leveraged or utilized when the various sensors and other devices as shown in FIG. 4 are not continuously monitoring and reporting data to the IRTA service 220 of the PTR 401. Additionally, the frequency of the data acquisition might be defined based upon the habits and/or mobility of the individual ultimately being monitored. For example, it might be justifiable to acquire data at a "10 minute interval" when the individual 426 is seventy (70) years old, but might not be justifiable when the individual 426 is eighty-five (85) years old. Here, it might be more appropriate to acquire data at a "1 minute interval" as mentioned above as an example. It is however contemplated that the length of the interval is configurable and may be defined as desired. Further, it is contemplated that data acquisition may be performed "on-demand." For example, if it determined that the individual 426 has been in the stairwell 412 for an unusual amount of time, a camera or the like might be remotely commanded to inspect the stairwell 412 to determine if the individual 426 has fallen down, etc. Such a feature is discussed in further detail below in connection with FIG. 6.

The Authorizations field may be selected to highlight that field, or place that field in-focus, to enable the viewer to define a various authentication codes or authorizations in accordance with the present disclosure. For example, upon initial access of the configuration interface 518, the viewer may define an alphanumeric sequence such as a PIN number, or the like, that may be entered upon access of the control selection 508 in a manner as discussed above. As another example, the viewer may define a telephone number that may be analyzed by the IRTA service 220 of the PTR 401 in order to make an initial determination as to whether or not a particular calling party is authorized to access and interact with the IRTA service 220 of the PTR 401, in order to enable the calling party to investigate the status of the individual 426 within the residence 404, in a manner similar to that as discussed above in connection with FIG. 1.

Such an implementation may be beneficial and/or advantageous in many respects. For example, it will be appreciated that it may be generally undesirable to allow or permit an unknown entity from accessing the IRTA service 220 of the PTR 401 to determine whether or not individual 426 is "at-home." For example, if an unknown entity did obtain such information, that information could be used to unlawfully enter the residence 404 when particular individual is not there. In this manner, the Authorizations field may be utilized to implement a number of security measures to prevent unauthorized access to the systems and method of the present disclosure.

The Emergency Response field may be selected to highlight that field, or place that field in-focus, as shown by intermittent line in FIG. 5, to enable the viewer to define a particular code to initiate an emergency response, and a particular code to bypass that option altogether in a manner similar to that discussed above in connection with FIG. 1. For example, a particular code to initiate an emergency response may be defined as "999"; whereas a particular code to bypass the emergency response option may be defined as "111." Additionally, the Emergency Response field may enable the viewer to define one or more actions to be instantiated by the IRTA service 220 of the PTR 401 in response to activation of the above-mentioned emergency response. For example, when defined in the Emergency Response field, the IRTA service 220 of the PTR 401 may instantiate a "911" telephone call, so as to notify emergency services and/or first responders of a possible emergency at the residence 404. As another example, when defined in the Emergency Response field, the IRTA service 220 of the PTR 401 may instantiate a text message to be sent to a particular phone number "303.111.1111" so as to notify at least one other individual, such as a family member or neighbor, of a possible emergency at the residence 404. As yet another example, when defined in the Emergency Response field, the IRTA service 220 of the PTR 401 may instantiate a message to be displayed on the television 214*c* itself, via the PTR 210, so as to notify at least one other individual, such as a family member or neighbor, of a possible emergency at the residence 404.

Following access of the various fields of the configuration interface 518 in order to define various parameters in a manner as described, it is contemplated that the viewer may manipulate the cursor 504 to select an enable selection 520 as shown in FIG. 5. Here, it is contemplated that in response to selection of the enable selection 520, the IRTA service 220 of the PTR 210 may generate and store a particular configuration profile 522 that includes data consistent with that entered into the configuration interface 518. Then, at a subsequent time, possibly upon establishment of a communication link between the PTR 210 and the PTR 401, as shown in FIG. 5, transfer the particular configuration profile 522 to the PTR 401. Here, it is contemplated that the IRTA service 220 of the PTR 401 may discover the particular configuration profile 522 and then program itself, the IRTA service 220, to function in a manner consistent with that as defined in the particular configuration profile 522. Additionally, in some instances, the particular configuration profile 522 may be stored to the server 218 of FIG. 2 as a back-up so that in event that the particular configuration profile 522 is corrupted, or in event of system error, associated with the PTR 401, or any system or device connected thereto within the residence 404, etc., the particular configuration profile 522 may be pushed down to the IRTA service 220 of the PTR 401 from the server 218 in effort to mitigate the situation.

Figure 6:
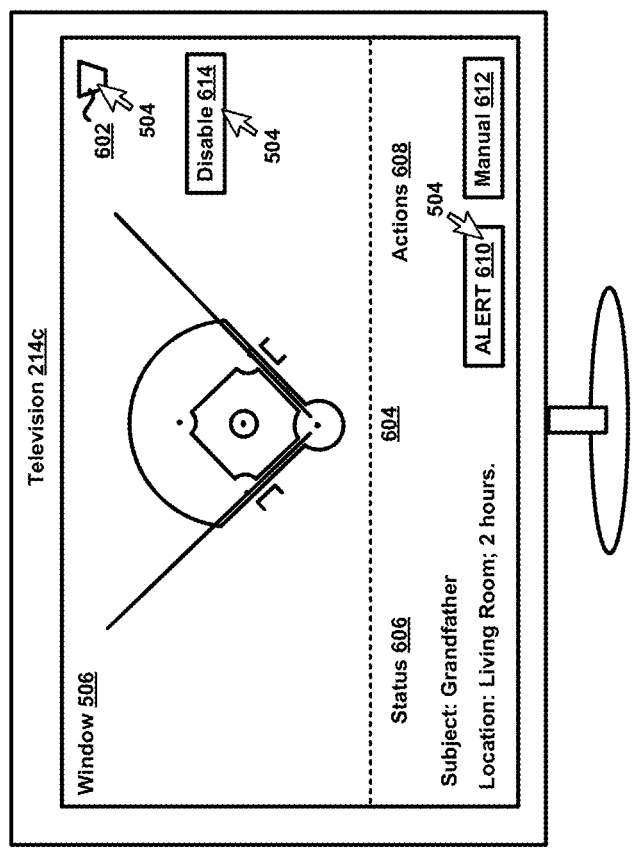
FIG. 6 shows third example aspects of the system of FIG. 2 in detail.

Referring now to FIG. 6, third example aspects of the system 200 of FIG. 2 are shown in detail. In particular, the television 214*c* is shown wherein the World Series is displayed for immediate viewing within the window 506, consistent with the above-description in connection with FIG. 5. Here, it is contemplated that the viewer mentioned above may manipulate the cursor 504 to select a discretely-positioned control 602 in order to access a fly-out window 604. Here, when the control 602 is subsequently selected, the window 604 may "collapse" so that any underling content displayed within the window is unobstructed, that which may be obstructed when the window 604 is in an "uncollapsed" state as shown in FIG. 6. In this example, the window 604 is shown to include a status section 606 and an actions section 608.

In general, the status section 606 may include or otherwise provide a condensed status summary of the individual 426 within the residence 404, who is discussed above in connection with FIG. 4. For example, the status section 606 may indicate "Subject: Grandfather; Location" Living Room; 2 hours." It is contemplated that such information may be populated and continuously or at least intermittently updated within the window 604 by the IRTA service 220 of the PTR 210, which itself may receive such and other information from the IRTA service 220 of the PTR 401 via network communication connection. Here, it is contemplated that essentially any information or data as acquired by the IRTA service 220 of the PTR 401 may be reported to the IRTA service 220 of the PTR 210 so that the status section 606 of the window 604 may be populated as desired. Further, it is contemplated that the information or data reported to the IRTA service 220 of the PTR 210 for output or display within the status section 606 may be configurable, defined as such via access of a reporting selection 528 as shown within the configuration interface 518 of FIG. 5.

In general, the actions section 606 may include or otherwise provide a means to instantiate an alert via interaction with the window 604, and a means to activate and command one or more systems, devices, sensors etc., selected from those shown and discussed above in connection with FIG. 4, via interaction with the window 604. For example, it is contemplated that the viewer may manipulate the cursor 504 to select an alert button 610, that when selected may command one or both of the IRTA service 220 of the PTR 401 and the IRTA service 220 of the PTR 210 to instantiate one or more emergency response actions consistent with that defined in the above-mentioned configuration profile 522, for example. Further, it is contemplated that the viewer may manipulate the cursor 504 to select a manual activation button 612, that when selected may command one or both of the IRTA service 220 of the PTR 401 and the IRTA service 220 of the PTR 210 to instantiate one or more actions to enable the viewer via the window 604 to access and remotely command a camera and/or speaker or microphone system positioned within the residence 404, for example, in order to visually and/or audibly inspect an area or location within the residence 404 to determine a status of the individual 426 as desired. Here, it is contemplated that functionality associated with the manual activation button 612 may be configurable, defined as such via access of a manual access selection 530 as shown within the configuration interface 518 of FIG. 5.

Figure 7:
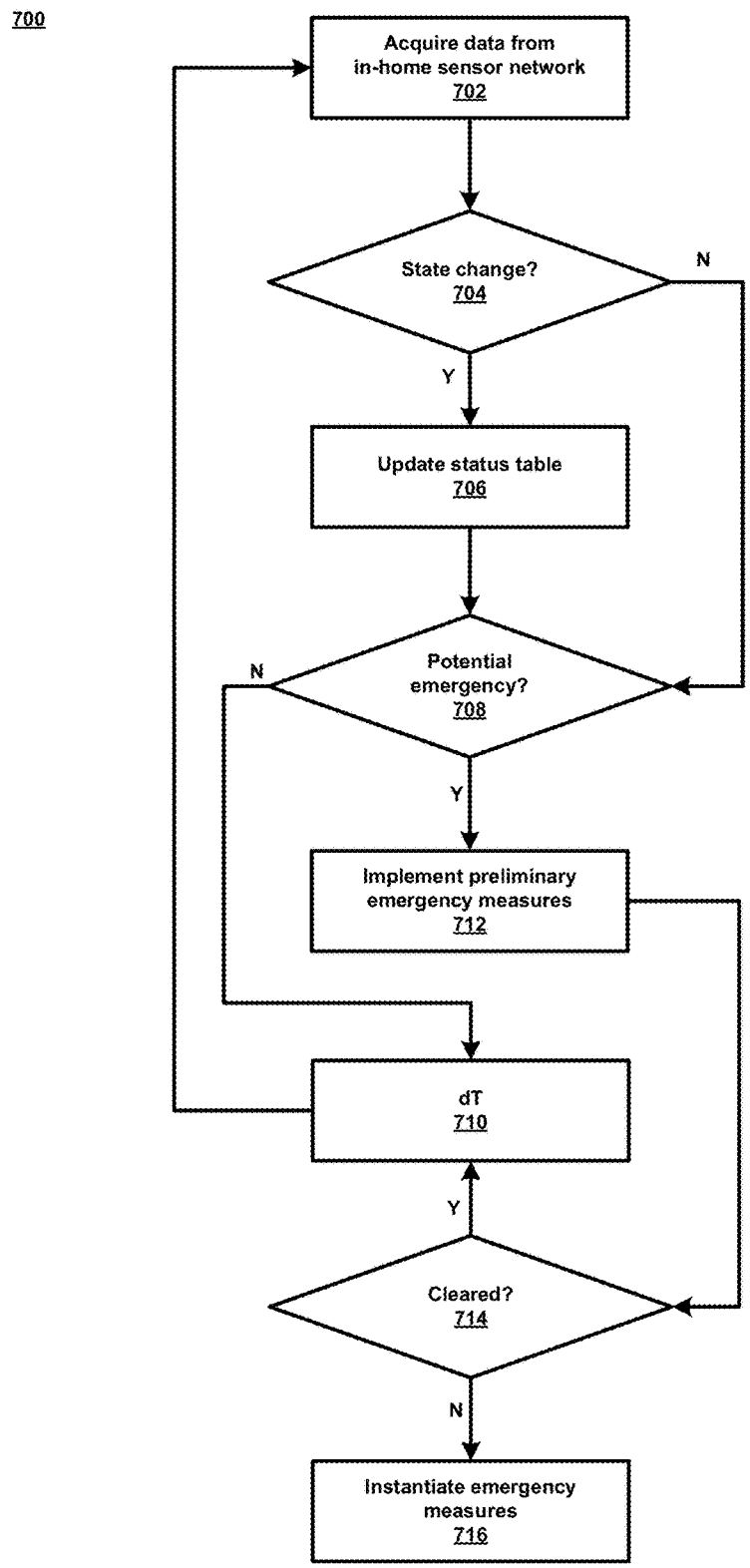
FIG. 7 shows a second example method according to the disclosure.

Referring now to FIG. 7, a second example method 700 is shown in accordance with the present disclosure. In particular, the method 700 may be implemented at least in part by the IRTA service 220 of the PTR 401, for example, as an optional or "opt-in" service to proactively, without direct or explicit inquiry (e.g. via phone), determine a "potential" or "probable" or "possible" status of the individual 426 within the residence 404. For example, at step 702, the IRTA service 220 may at an instant point in time query or otherwise activate each and every sensor 418 within the residence 404 to supply data in accordance with an associated particular sensor type. Next, at step 704, the IRTA service 220 may access a table or like data structure to determine whether or not there has been any state change since a time of previous query (step 102). For example, whether the oven has been turned on, the garage door open and then closed, and etc. If a state change has occurred, flow may proceed to step 706 where table or like data structure is updated or appended, etc., to reflect the change in state. Otherwise, flow may proceed to from step 704 directly to step 708.

At step 708, the IRTA service 220 may examine the table or like data structure as updated or appended, and also the same as immediately prior to the modification, if applicable, to make an estimation as to whether or not a potential emergency may exist. For example, if it had been previously determined that the individual 426 had been sitting in the chair 428 (see FIG. 4) at 7:00 PM, and at the same time the television 424 was "on," and then if it is newly determined that the individual 426 is still sitting in the chair 428 at 7:30 PM, and at the same time the television 424 is "on," then the IRTA service 220 may deduce that the individual 426 is OK and simply watching TV. In such a scenario, process flow may proceed to step 710, and then following passage of a predetermined time period dT, process flow may proceed to back to step 702.

However, if it had been previously determined that the individual 426 had been sitting in the chair at 7:00 PM, and at the same time the television 424 was "on," and then if it is newly determined that the individual 426 is lying on the ground immediately in front of the chair at 7:30 PM, and at the same time the television 424 is "on," then the IRTA service 220 may deduce that the individual 426 is not OK and might need assistance. In such a scenario, process flow may proceed to step 712, where a preliminary emergency measure may be taken or otherwise instantiated by the IRTA service 220. For example, a phone call may be placed by the IRTA service 220 to particular party with the message "Your Father might need assistance. Call immediately. A similar message may additionally, or alternatively, be populated into an email communication and/or text message communication and sent to one or more parties. Process flow may then proceed to step 714.

At step 714, a manual command may be received by the IRTA service 220 to clear the possible emergency. For example, the above-mentioned particular party or even the individual 426 may "disable" the initial alert as raised by the IRTA service 220 at step 712 by a particular command submitted to the IRTA service 220 via display interface (e.g., via disable button 614 as shown in FIG. 6) or via phone (e.g., bypass command 222 as shown in FIG. 5). If the initial alert as raised by the IRTA service 220 is in fact disabled, process flow may proceed to step 710, and then following passage of a predetermined time period dT, process flow may proceed to back to step 702. Otherwise, process flow may proceed to step 716 in which one or more predefined and user-configurable emergency measures may be implemented or otherwise instantiated by the IRTA service 220, in a manner similar to that as discussed above in connection with at least FIG. 1.

As mentioned above, the various features or aspects of the present disclosure are directed to or towards systems and methods for monitoring, via a network of sensors each communicatively coupled to a home gateway system, movement and location of one or more individuals within their own residence. The system may also respond to inquiries as to a potential or probable or possible status of the one or more individuals within the residence. For example, the system may exhibit any particular combination of special-purpose firmware, software, and/or hardware, to enable the system to accept and process signals from a telephony system, that of which may be considered an originating source of the inquiry, and also to enable an inquiring individual or calling party to interact with the system in order to investigate the status of the one or more individuals within the residence. The various features or aspects of the present disclosure may be incorporated into or within a television receiver as part of a satellite television implementation. This may, among other things, serve to entice new customers to subscribe to services as offered by a particular satellite television provider, as well as provide an incentive for existing customers to maintain their loyalty and/or relationship with the particular satellite television provider. These and other benefits and/or advantages may be realized in a number of different ways, including by one or more of the systems, devices, methods, computer-program products, etc., of the present disclosure.

Figure 8:
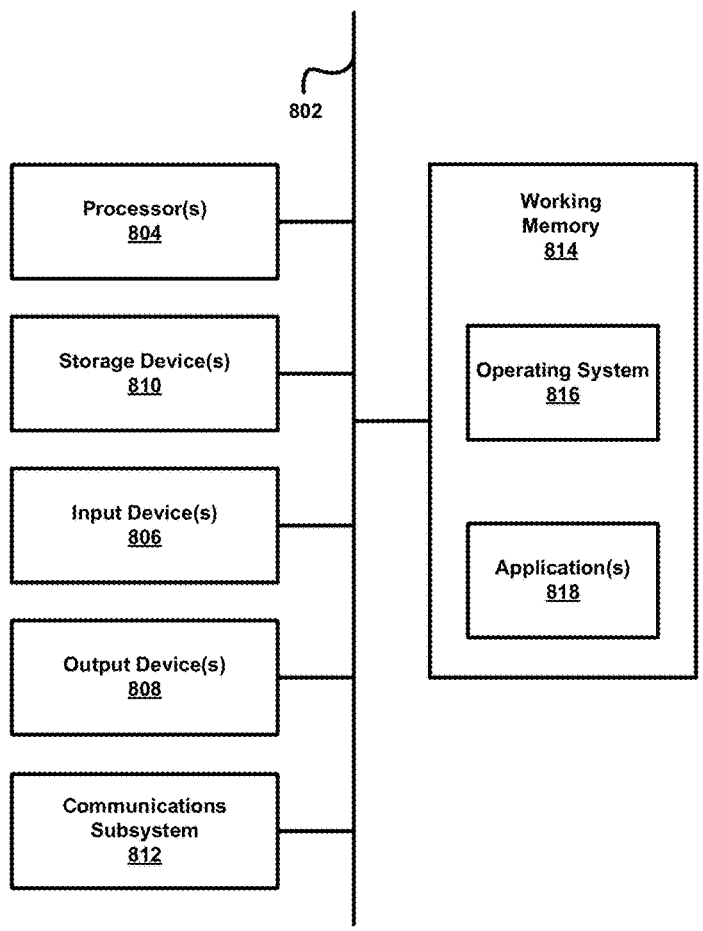
FIG. 8 shows an example computing system or device.

FIG. 8 shows an example computer system or device 800 in accordance with the disclosure. An example of a computer system or device includes an enterprise server, blade server, desktop computer, laptop computer, tablet computer, personal data assistant, smartphone, gaming console, STB, television receiver, and/or any other type of machine configured for performing calculations. Any particular one of the previously-described computing devices may be wholly or at least partially configured to exhibit features similar to the computer system 800, such as any of the respective elements of at least FIG. 2. In this manner, any of one or more of the respective elements of at least FIG. 2 may be configured and/or arranged, wholly or at least partially, to enable for monitoring, via a network of sensors each communicatively coupled to a home gateway system, the movement and location of one or more individuals within their own residence, and also associated with responding to inquiries as to a potential or probable or possible status of the one or more individuals within the residence, in manner consistent with that discussed above in connection with FIGS. 1-7. For example, any of one or more of the respective elements of at least FIG. 2 may be configured and/or arranged to perform and/or include instructions that, when executed, perform the method of FIG. 1 and/or FIG. 7. Still further, any of one or more of the respective elements of at least FIG. 2 may be configured to perform and/or include instructions that, when executed, instantiate and implement functionality of the PTR 210 and/or the computing devices 216*a-b* and/or the server(s) 218 of FIG. 2.

The computer device 800 is shown comprising hardware elements that may be electrically coupled via a bus 802 (or may otherwise be in communication, as appropriate). The hardware elements may include a processing unit with one or more processors 804, including without limitation one or more general-purpose processors and/or one or more special-purpose processors (such as digital signal processing chips, graphics acceleration processors, and/or the like); one or more input devices 806, which may include without limitation a remote control, a mouse, a keyboard, and/or the like; and one or more output devices 808, which may include without limitation a presentation device (e.g., television), a printer, and/or the like.

The computer system 800 may further include (and/or be in communication with) one or more non-transitory storage devices 810, which may comprise, without limitation, local and/or network accessible storage, and/or may include, without limitation, a disk drive, a drive array, an optical storage device, a solid-state storage device, such as a random access memory, and/or a read-only memory, which may be programmable, flash-updateable, and/or the like. Such storage devices may be configured to implement any appropriate data stores, including without limitation, various file systems, database structures, and/or the like.

The computer device 800 might also include a communications subsystem 812, which may include without limitation a modem, a network card (wireless and/or wired), an infrared communication device, a wireless communication device and/or a chipset such as a Bluetooth™ device, 802.11 device, WiFi device, WiMax device, cellular communication facilities such as GSM (Global System for Mobile Communications), W-CDMA (Wideband Code Division Multiple Access), LTE (Long Term Evolution), etc., and/or the like. The communications subsystem 812 may permit data to be exchanged with a network (such as the network described below, to name one example), other computer systems, and/or any other devices described herein. In many examples, the computer system 800 will further comprise a working memory 814, which may include a random access memory and/or a read-only memory device, as described above.

The computer device 800 also may comprise software elements, shown as being currently located within the working memory 814, including an operating system 816, device drivers, executable libraries, and/or other code, such as one or more application programs 818, which may comprise computer programs provided by various examples, and/or may be designed to implement methods, and/or configure systems, provided by other examples, as described herein. By way of example, one or more procedures described with respect to the method(s) discussed above, and/or system components might be implemented as code and/or instructions executable by a computer (and/or a processor within a computer); in an aspect, then, such code and/or instructions may be used to configure and/or adapt a general purpose computer (or other device) to perform one or more operations in accordance with the described methods.

A set of these instructions and/or code might be stored on a non-transitory computer-readable storage medium, such as the storage device(s) 810 described above. In some cases, the storage medium might be incorporated within a computer system, such as computer system 800. In other examples, the storage medium might be separate from a computer system (e.g., a removable medium, such as flash memory), and/or provided in an installation package, such that the storage medium may be used to program, configure, and/or adapt a general purpose computer with the instructions/code stored thereon. These instructions might take the form of executable code, which is executable by the computer device 800 and/or might take the form of source and/or installable code, which, upon compilation and/or installation on the computer system 800 (e.g., using any of a variety of generally available compilers, installation programs, compression/decompression utilities, etc.), then takes the form of executable code.

It will be apparent that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, in one aspect, some examples may employ a computer system (such as the computer device 800) to perform methods in accordance with various examples of the disclosure. According to a set of examples, some or all of the procedures of such methods are performed by the computer system 800 in response to processor 804 executing one or more sequences of one or more instructions (which might be incorporated into the operating system 816 and/or other code, such as an application program 818) contained in the working memory 814. Such instructions may be read into the working memory 814 from another computer-readable medium, such as one or more of the storage device(s) 810. Merely by way of example, execution of the sequences of instructions contained in the working memory 814 may cause the processor(s) 804 to perform one or more procedures of the methods described herein.

The terms "machine-readable medium" and "computer-readable medium," as used herein, may refer to any non-transitory medium that participates in providing data that causes a machine to operate in a specific fashion. In an embodiment implemented using the computer device 800, various computer-readable media might be involved in providing instructions/code to processor(s) 804 for execution and/or might be used to store and/or carry such instructions/code. In many implementations, a computer-readable medium is a physical and/or tangible storage medium. Such a medium may take the form of a non-volatile media or volatile media. Non-volatile media may include, for example, optical and/or magnetic disks, such as the storage device(s) 810. Volatile media may include, without limitation, dynamic memory, such as the working memory 814.

Example forms of physical and/or tangible computer-readable media may include a floppy disk, a flexible disk, hard disk, magnetic tape, or any other magnetic medium, a compact disc, any other optical medium, ROM (Read Only Memory), RAM (Random Access Memory), and etc., any other memory chip or cartridge, or any other medium from which a computer may read instructions and/or code. Various forms of computer-readable media may be involved in carrying one or more sequences of one or more instructions to the processor(s) 804 for execution. By way of example, the instructions may initially be carried on a magnetic disk and/or optical disc of a remote computer. A remote computer might load the instructions into its dynamic memory and send the instructions as signals over a transmission medium to be received and/or executed by the computer system 800.

The communications subsystem 812 (and/or components thereof) generally will receive signals, and the bus 802 then might carry the signals (and/or the data, instructions, etc. carried by the signals) to the working memory 814, from which the processor(s) 804 retrieves and executes the instructions. The instructions received by the working memory 814 may optionally be stored on a non-transitory storage device 810 either before or after execution by the processor(s) 804.

It should further be understood that the components of computer device 800 can be distributed across a network. For example, some processing may be performed in one location using a first processor while other processing may be performed by another processor remote from the first processor. Other components of computer system 800 may be similarly distributed. As such, computer device 800 may be interpreted as a distributed computing system that performs processing in multiple locations. In some instances, computer system 800 may be interpreted as a single computing device, such as a distinct laptop, desktop computer, or the like, depending on the context.

The methods, systems, and devices discussed above are examples. Various configurations may omit, substitute, or add various method steps or procedures, or system components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those of skill with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations may be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Furthermore, the example examples described herein may be implemented as logical operations in a computing device in a networked computing system environment. The logical operations may be implemented as: (i) a sequence of computer implemented instructions, steps, or program modules running on a computing device; and (ii) interconnected logic or hardware modules running within a computing device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method, comprising:
   detecting, by a television receiver, a command to display programming from a television provider;
   receiving, by the television receiver, a data signal corresponding to the programming;
   outputting, by the television receiver for display by a display device, a first audio-video output signal including the programming;
   outputting, by the television receiver for display by the display device, a second audio-video output signal corresponding to a user interface including options relating to reporting of a status of an individual associated with a residence including the television receiver;
   receiving, by the television receiver, input corresponding to a change in the options;
   modifying, by the television, a configuration of the television receiver according to the change in the options;
   receiving, by the television receiver, a configuration profile from a remote television receiver, wherein the configuration profile relates to reporting of the status of the individual associated with the residence;
   modifying, by the television, the configuration of the television receiver according to the configuration profile;
   detecting, by the television receiver, an in-bound telephone call from a calling device that is different from the remote television receiver;
   determining, by the television receiver, that a calling party associated with the in-bound telephone call is authorized to access a message that provides an indication of the status of the individual associated with the residence including the television receiver, wherein the television receiver serves as a gateway of a home automation system of the residence;
   retrieving, by the television receiver, data from a number of sensors associated with the home automation system and positioned within the residence;
   deriving, by the television receiver, the status of the individual using the data;
   determining, by the television receiver, the message that provides the indication of the status of the individual;
   playing-back, by the television receiver for the calling party, the message that provides the indication of the status of the individual;
   detecting, by the television receiver, input corresponding to a selection made by the calling party to instantiate an emergency response alert;
   instantiating, by the television receiver, the emergency response alert;
   transmitting, by the television receiver, a notification to the remote television receiver for display of the notification on a remote display device associated with the remote television receiver, wherein the notification includes the status of the individual;
   detecting, by the television receiver, an additional in-bound telephone call from an additional calling device that is different from the remote television receiver;
   determining, by the television receiver, that an additional calling party of the additional in-bound telephone call is unauthorized to access the message; and
   rolling, by the television receiver, the additional in-bound telephone call to voicemail.

2. The method of claim 1, further comprising:
   prompting the calling party to enter a passcode to determine whether the calling party is authorized to access the message.

3. The method of claim 1, further comprising:
   analyzing a telephone number associated with the in-bound telephone call to determine whether the calling party is authorized to access the message.

4. The method of claim 1, further comprising:
   answering, by the television receiver, the in-bound telephone call following a particular ring count.

5. The method of claim 1, further comprising:
   retrieving, by the television receiver, additional data from sensors associated with the home automation system and positioned external to the residence, wherein deriving the status of the individual includes deriving the status of the individual using the data and the additional data.

6. The method of claim 1, wherein determining the message includes identifying data from at least one of the sensors to include as at least a portion of content of the message.

7. The method of claim 1, further comprising:
   periodically generating, by the television receiver, content for insertion into the message based on data retrieved by the television receiver from each of the number of sensors.

8. The method of claim 1, further comprising:
   generating, by the television receiver in response to a command received by the television receiver over a network connection from a remote television receiver, content for insertion into the message based on data retrieved by the television receiver from each of the number of sensors.

9. The method of claim 1, further comprising:
   receiving, by the television receiver, a definition to authorize the calling party to access the message; and
   storing the definition to a persistent storage medium of the television receiver.

10. The method of claim 1, wherein the emergency response alert includes disabling or turning off one or more appliances at the residence to address a possible emergency situation at the residence.

11. A television receiver, comprising:
    at least one processor;
    a network interface communicatively coupled with the at least one processor and operable to establish network connections with sensors associated with a home automation system of a residence;
    an output interface communicatively coupled with the at least one processor and operable to generate audio-video output signals for use by display devices; and
    at least one memory element communicatively coupled with and readable by the at least one processor and having stored therein processor-readable instructions that, when executed by the at least one processor, cause the at least one processor to perform operations including:
      detecting a command to display programming from a television provider;
      receiving a data signal corresponding to the programming;
      outputting a first audio-video output signal including the programming using the output interface;

outputting a second audio-video output signal using the output interface, wherein the second audio-video output signal corresponds to a user interface including options relating to reporting of a status of an individual associated with the residence, the residence including the television receiver;

receiving input corresponding to a change in the options;

modifying a configuration of the television receiver according to the change in the options;

receiving a configuration profile from a remote television receiver, wherein the configuration profile relates to reporting of the status of the individual associated with the residence;

modifying the configuration of the television receiver according to the configuration profile;

detecting an in-bound telephone call from a calling device that is different from the remote television receiver;

determining that a calling party associated with the in-bound telephone call is authorized to access a message that provides an indication of the status of the individual associated with the residence including the television receiver, wherein the television receiver serves as a gateway of the home automation system of the residence;

retrieving data from a number of sensors associated with the home automation system and positioned within the residence;

deriving the status of the individual using the data;

determining the message that provides the indication of the status of the individual; and playing-back, for the calling party, the message that provides the indication of the status of the individual;

detecting input corresponding to a selection made by the calling party to instantiate an emergency response alert;

instantiating the emergency response alert;

transmitting a notification to the remote television receiver for display of the notification on a remote display device associated with the remote television receiver, wherein the notification includes the status of the individual;

detecting an additional in-bound telephone call from an additional calling device that is different from the remote television receiver; and determining that an additional calling party of the additional in-bound telephone call is unauthorized to access the message; and rolling the additional in-bound telephone call to voicemail.

12. The television receiver of claim 11, wherein deriving the status of the individual includes:
identifying a first state associated with the number of sensors at a first time;
identifying a second state associated with the number of sensors at a second time after the first time; and
determining a change between the first state and the second state, wherein the change is associated with the status of the individual.

13. The television receiver of claim 11, wherein the operations further include:
prompting the calling party to enter a passcode to determine whether the calling party is authorized to access the message.

14. The television receiver of claim 11, wherein the operations further include:
analyzing a telephone number associated with the in-bound telephone call to determine whether the calling party is authorized to access the message.

15. The television receiver of claim 11, wherein the operations further include:
answering the in-bound telephone call following a particular ring count.

16. The television receiver of claim 11, wherein the operations further include:
transmitting, to a remote television receiver, an indicator of the status of the individual;
receiving, from the remote television receiver, a command to obtain additional sensor data from one or more of the number of sensors; and
transmitting the additional sensor data to the remote television receiver.

17. The television receiver of claim 11, wherein the operations further include:
generating, in response to a command received by the television receiver from a remote television receiver over a network connection, content for insertion into the message based on data retrieved by the television receiver from each of the number of sensors.

18. A method, comprising:
detecting, by a television receiver, a command to display programming from a television provider;
receiving, by the television receiver, a data signal corresponding to the programming;
outputting, by the television receiver for display by a display device, an audio-video output signal including the programming;
outputting, by the television receiver for display by the display device, a second audio-video output signal corresponding to a user interface including options relating to reporting of a status of an individual associated with a residence including the television receiver;
receiving, by the television receiver, input corresponding to a change in the options;
modifying, by the television, a configuration of the television receiver according to the change in the options;
receiving, by the television receiver, a configuration profile from a remote television receiver, wherein the configuration profile relates to reporting of the status of the individual associated with the residence;
modifying, by the television, the configuration of the television receiver according to the configuration profile;
detecting, by the television receiver, an in-bound telephone call from a calling device that is different from the remote television receiver;
analyzing, by the television receiver, a telephone number associated with the in-bound telephone call as a primary security measure to determine whether a calling party associated with the in-bound telephone call is authorized to access a message that provides an indication of a status of an individual associated with a residence including the television receiver, wherein the television receiver serves as a gateway of a home automation system of the residence;
authenticating, by the television receiver, the telephone number to determine that the calling party is authorized to access a secondary security measure to determine whether the calling party is authorized to access a message;

receiving, by the television receiver, input corresponding to a determination of a passcode entered by the calling party;

analyzing, by the television receiver, the passcode entered as the secondary security measure to determine whether the calling party is authorized to access the message;

authenticating, by the television receiver, the passcode to determine that the calling party is authorized to access the message;

retrieving, by the television receiver, data from a number of sensors associated with the home automation system and positioned within the residence;

deriving, by the television receiver, the status of the individual based upon the data;

determining, by the television receiver, the message that provides the indication of the status of the individual;

playing-back, by the television receiver for the calling party, the message that provides the indication of the status of the individual;

detecting, by the television receiver, input corresponding to a selection made by the calling party to instantiate an emergency response alert;

instantiating, by the television receiver, the emergency response alert transmitting, by the television receiver, a notification to the remote television receiver for display of the notification on a remote display device associated with the remote television receiver, wherein the notification includes the status of the individual;

detecting, by the television receiver, an additional in-bound telephone call from an additional calling device that is different from the remote television receiver;

determining, by the television receiver, that an additional calling party of the additional in-bound telephone call is unauthorized to access the message; and rolling, by the television receiver, the additional in-bound telephone call to voicemail.

19. The method of claim 18, wherein determining the message includes identifying data from at least one of the sensors to include as at least a portion of content of the message.

20. The method of claim 18, wherein deriving the status of the individual includes identifying a location of the individual within the residence using data from at least one of the sensors; and wherein the message includes the location.

* * * * *